US 10,561,370 B2

(12) United States Patent
Salazar et al.

(10) Patent No.: US 10,561,370 B2
(45) Date of Patent: Feb. 18, 2020

(54) APPARATUS TO SECURE FIELD GENERATING DEVICE TO CHAIR

(71) Applicants: Acclarent, Inc., Irvine, CA (US); Biosense Webster (Israel) Ltd., Yokneam (IL)

(72) Inventors: Henry F. Salazar, Pico Rivera, CA (US); Jetmir Palushi, Irvine, CA (US); William J. Kane, Newport Coast, CA (US); Fatemeh Akbarian, Rancho Palos Verdes, CA (US); Ika Dekel, Yokneam (IL); Noam Racheli, Hadera (IL); Helen Wolfson, Haifa (IL); Nawid Mehrzai, Mission Viejo, CA (US); Jephrey S. Rodriguez, Placentia, CA (US); Ketan P. Muni, San Jose, CA (US); Andrew Drake, San Francisco, CA (US); David A. Smith, Jr., Lake Forest, CA (US); Scott A. Kirchner, Irvine, CA (US); Todd A. Veloni, Lake Forest, CA (US); Itamar Bustan, Zichron Ya'acov (IL)

(73) Assignees: Acclarent, Inc., Irvine, CA (US); Biosense Webster (Israel) Ltd., Yokneam (IL)

(*) Notice: Subject to any disclaimer, the term of this patent is extended or adjusted under 35 U.S.C. 154(b) by 85 days.

(21) Appl. No.: 15/933,737

(22) Filed: Mar. 23, 2018

(65) Prior Publication Data
US 2018/0310886 A1   Nov. 1, 2018

Related U.S. Application Data

(60) Provisional application No. 62/490,241, filed on Apr. 26, 2017, provisional application No. 62/555,824, filed on Sep. 8, 2017.

(51) Int. Cl.
*A61B 5/00* (2006.01)
*A61B 6/04* (2006.01)
(Continued)

(52) U.S. Cl.
CPC .............. *A61B 5/702* (2013.01); *A61B 5/062* (2013.01); *A61B 6/0478* (2013.01); *A61G 13/121* (2013.01); *A61B 2034/2051* (2016.02)

(58) Field of Classification Search
None
See application file for complete search history.

(56) References Cited

U.S. PATENT DOCUMENTS 6,021,343 A * 2/2000 Foley ..................... A61B 17/16
600/417
6,366,799 B1 * 4/2002 Acker ..................... A61B 5/06
600/424
(Continued)

OTHER PUBLICATIONS

U.S. Appl. No. 62/453,220, entitled "Navigation Guidewire with Interlocked Coils," filed Feb. 1, 2017.
(Continued)

*Primary Examiner* — David E Allred
(74) *Attorney, Agent, or Firm* — Frost Brown Todd LLC

(57) ABSTRACT

An apparatus includes a body, an upright member, a frame, and a plurality of field generating elements. The body is configured to be positioned between a patient's back and a backrest of a chair. The upright member extends upwardly from the body. The frame has a curved configuration configured to partially surround a patient's head. The field generating elements are configured to generate an electromagnetic field around a patient's head partially surrounded by the frame.

16 Claims, 37 Drawing Sheets

(51) Int. Cl.
*A61B 5/06* (2006.01)
*A61G 13/12* (2006.01)
*A61B 34/20* (2016.01)

(56) References Cited

U.S. PATENT DOCUMENTS

| | | | | |
|---|---|---|---|---|
| 7,204,557 | B1* | 4/2007 | Burton | A47O 7/383 |
| | | | | 297/397 |
| 7,720,521 | B2 | 5/2010 | Chang et al. | |
| 8,123,722 | B2 | 2/2012 | Huang et al. | |
| 8,190,389 | B2 | 5/2012 | Kim et al. | |
| 8,320,711 | B2 | 11/2012 | Altmann et al. | |
| 8,702,626 | B1 | 4/2014 | Kim et al. | |
| 8,740,307 | B1* | 6/2014 | Thomas | B60N 2/882 |
| | | | | 297/397 |
| 8,777,926 | B2 | 7/2014 | Chang et al. | |
| 8,850,642 | B2* | 10/2014 | Rasmussen | A47G 9/1027 |
| | | | | 297/398 |
| 9,095,646 | B2 | 8/2015 | Chow et al. | |
| 9,155,492 | B2 | 10/2015 | Jenkins et al. | |
| 9,167,961 | B2 | 10/2015 | Makower et al. | |
| 9,198,736 | B2 | 12/2015 | Kim et al. | |
| 2005/0049486 | A1* | 3/2005 | Urquhart | A61B 90/14 |
| | | | | 600/429 |
| 2007/0208252 | A1 | 9/2007 | Makower | |
| 2008/0183128 | A1 | 7/2008 | Morriss et al. | |
| 2008/0269588 | A1* | 10/2008 | Csavoy | A61B 6/5247 |
| | | | | 600/407 |
| 2010/0030031 | A1 | 2/2010 | Goldfarb et al. | |
| 2010/0081914 | A1* | 4/2010 | Waynik | A61B 34/20 |
| | | | | 600/407 |
| 2011/0004057 | A1 | 1/2011 | Goldfarb et al. | |
| 2011/0060214 | A1 | 3/2011 | Makower | |
| 2012/0071857 | A1 | 3/2012 | Goldfarb et al. | |
| 2014/0074141 | A1 | 3/2014 | Johnson et al. | |
| 2014/0200444 | A1 | 7/2014 | Kim et al. | |
| 2014/0364725 | A1 | 12/2014 | Makower | |
| 2016/0008083 | A1 | 1/2016 | Kesten et al. | |
| 2016/0310042 | A1 | 10/2016 | Kesten et al. | |
| 2016/0310714 | A1 | 10/2016 | Jenkins et al. | |
| 2017/0120020 | A1 | 5/2017 | Lin et al. | |
| 2017/0320413 | A1* | 11/2017 | Knapp | B60N 2/882 |
| 2018/0110567 | A1* | 4/2018 | Amit | A61B 34/20 |

OTHER PUBLICATIONS

U.S. Appl. No. 62/490,241, entitled "Apparatus to Secure Field Generating Device to Chair," filed Apr. 26, 2017.
U.S. Appl. No. 62/555,824, entitled "Apparatus to Secure Field Generating Device to Chair," filed Sep. 8, 2017.

* cited by examiner

APPARATUS TO SECURE FIELD GENERATING DEVICE TO CHAIR

This application claims priority to U.S. Provisional Pat. App. No. 62/490,241, entitled "Apparatus to Secure Field Generating Device to Chair," filed Apr. 26, 2017, the disclosure of which is incorporated by reference herein.

BACKGROUND

This application also claims priority to U.S. Provisional Pat. App. No. 62/555,824, entitled "Apparatus to Secure Field Generating Device to Chair," filed Sep. 8, 2017, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or Mill, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2 dimensional, line-of-sight view. The use of image guidance systems provides a real time, 3-dimensional view of all of the anatomy surrounding the operative field, not just that which is actually visible in the spatially limited, 2 dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
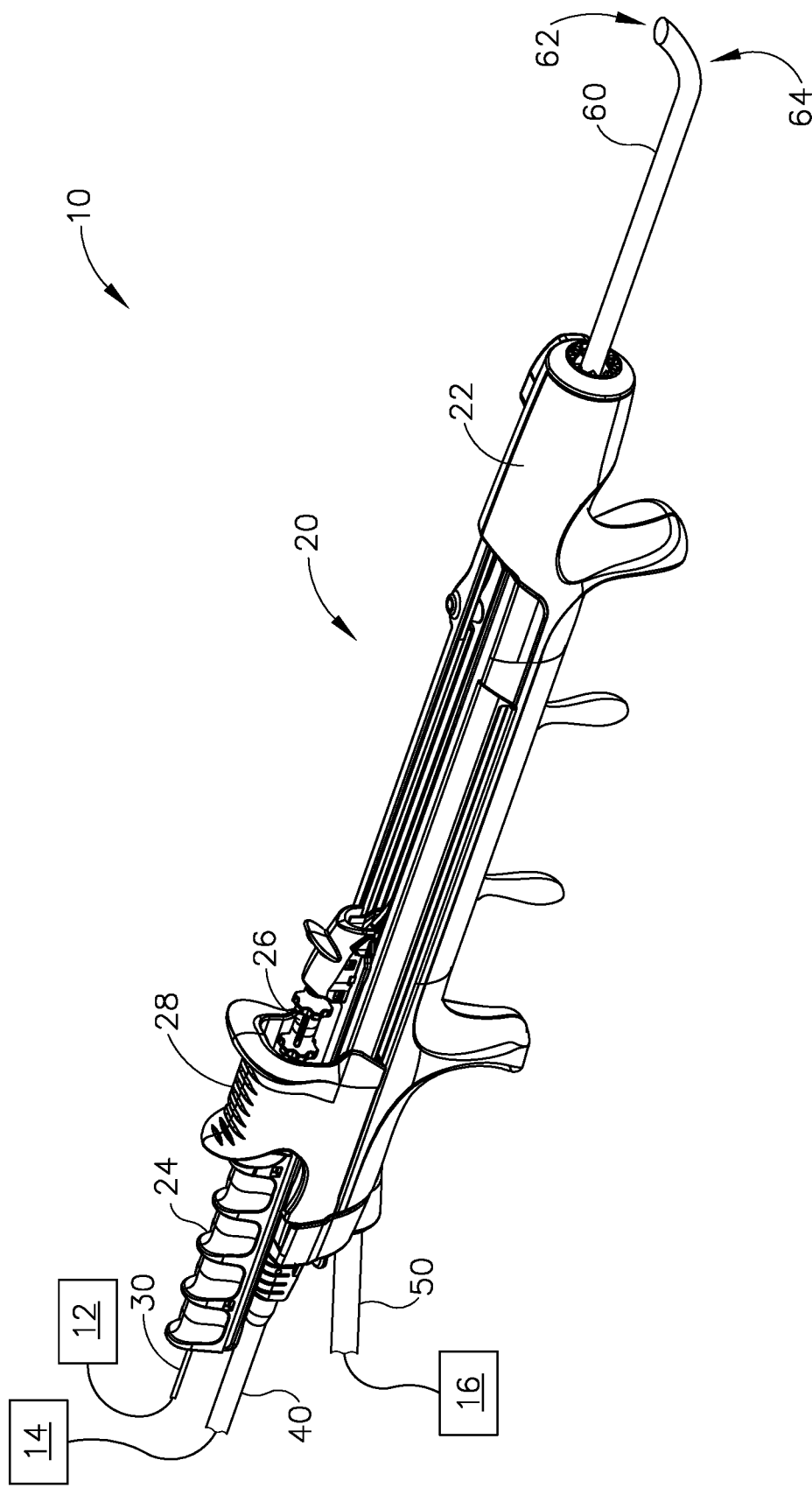
FIG. 1A depicts a perspective view of an exemplary dilation instrument assembly, with a guidewire in a proximal position, and with a dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D shows an exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) comprises a source of light. In some other versions, guidewire power source (12) is part of an IGS system as described below. In the present example, inflation source (14) comprises a source of saline. However, it should be understood that any other suitable source of fluid (liquid or otherwise) may be used. Also in the present example, irrigation fluid source (16) comprises a source of saline. Again, though, any other suitable source of fluid may be used. It should also be understood that flush fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22). It should therefore be understood that dilation instrument (20) may be fully operated by a single hand of a human operator.

A. Exemplary Guide Catheter

A guide catheter (60) extends distally from handle body (22). Guide catheter (60) includes an open distal end (62) and a bend (64) formed proximal to open distal end (62). In the present example, dilation instrument (20) is configured to removably receive several different kinds of guide catheters (60), each guide catheter (60) having a different angle formed by bend (64). These different angles may facilitate access to different anatomical structures. Various examples of angles and associated anatomical structures are described in one or more of the references cited herein; while further examples will be apparent to those of ordinary skill in the art in view of the teachings herein. Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

B. Exemplary Guidewire

Figure 1B:
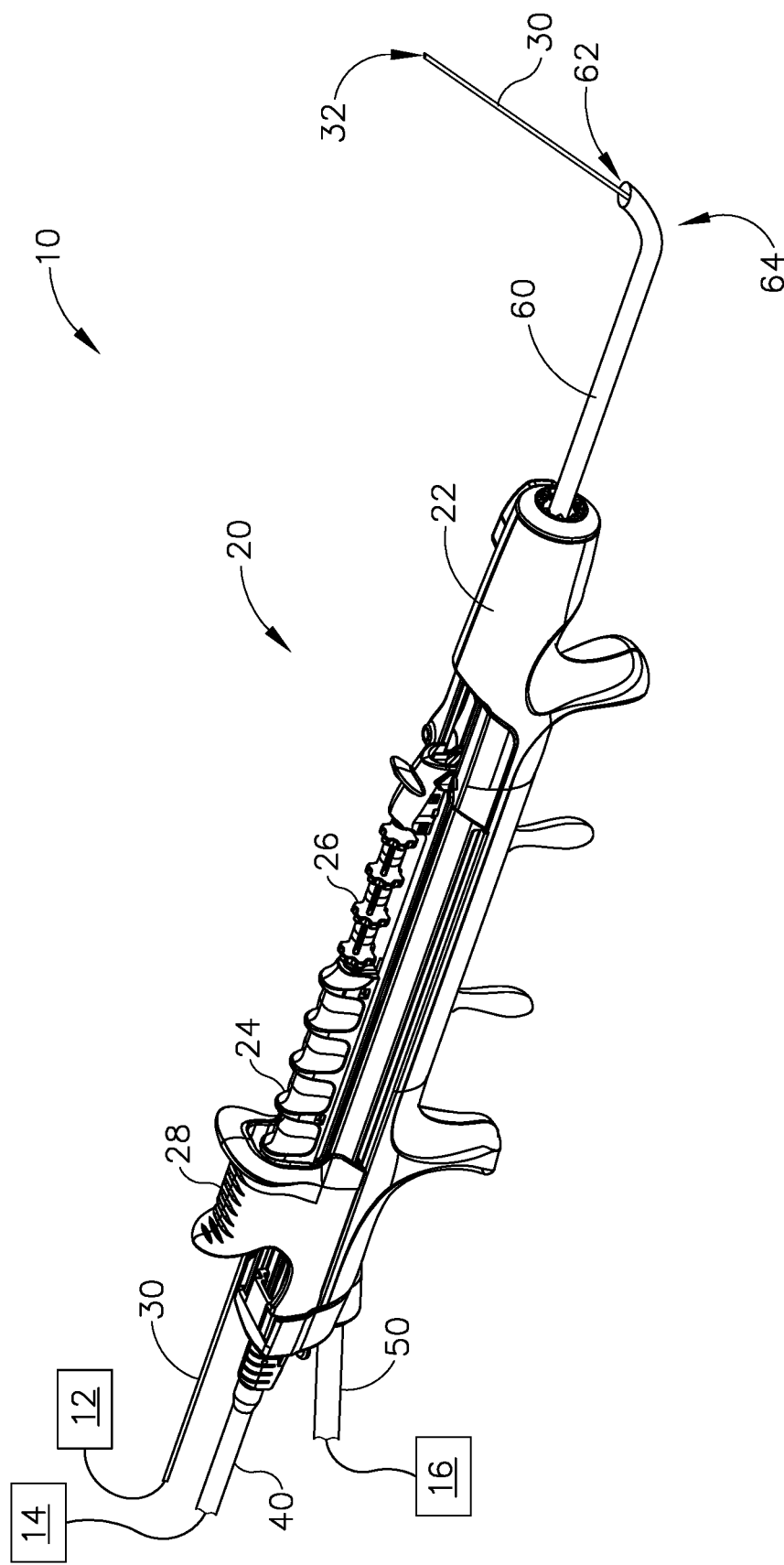
FIG. 1B depicts a perspective view of the dilation instrument assembly of FIG. 1A, with the guidewire in a distal position, and with the dilation catheter in the proximal position.

Dilation instrument (30) further comprises a guidewire (30), which is coaxially disposed in guide catheter (60). Guidewire slider (24) is secured to guidewire (30) such that translation of guidewire slider (24) relative to handle body (22) provides corresponding translation of guidewire (30) relative to handle body (22). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, guidewire (30) includes a preformed bend formed just proximal to the distal end (32) of guidewire (30). In such versions, the preformed bend and the rotatability provided via guidewire spinner (26) may facilitate alignment and insertion of distal end (32) into a sinus ostium, Eustachian tube, or other passageway to be dilated. Also in some versions, guidewire (30) includes at least one optical fiber extending to a lens or other optically transmissive feature in distal end (32). This optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure.

By way of example only, guidewire (30) may be configured in accordance with at least some of the teachings of U.S. Pat. No. 9,155,492, the disclosure of which is incorporated by reference herein. In some versions, guidewire

(30) is configured similar to the Relieva Luma Sentry™ Sinus Illumination System by Acclarent, Inc. of Irvine, Calif. In addition to, or as an alternative to, including one or more optical fibers, guidewire (30) may include a sensor and at least one wire that enables guidewire (30) to provide compatibility with an IGS system as described in greater detail below. Other features and operabilities that may be incorporated into guidewire (30) will be apparent to those of ordinary skill in the art in view of the teachings herein.

C. Exemplary Dilation Catheter

Figure 1C:
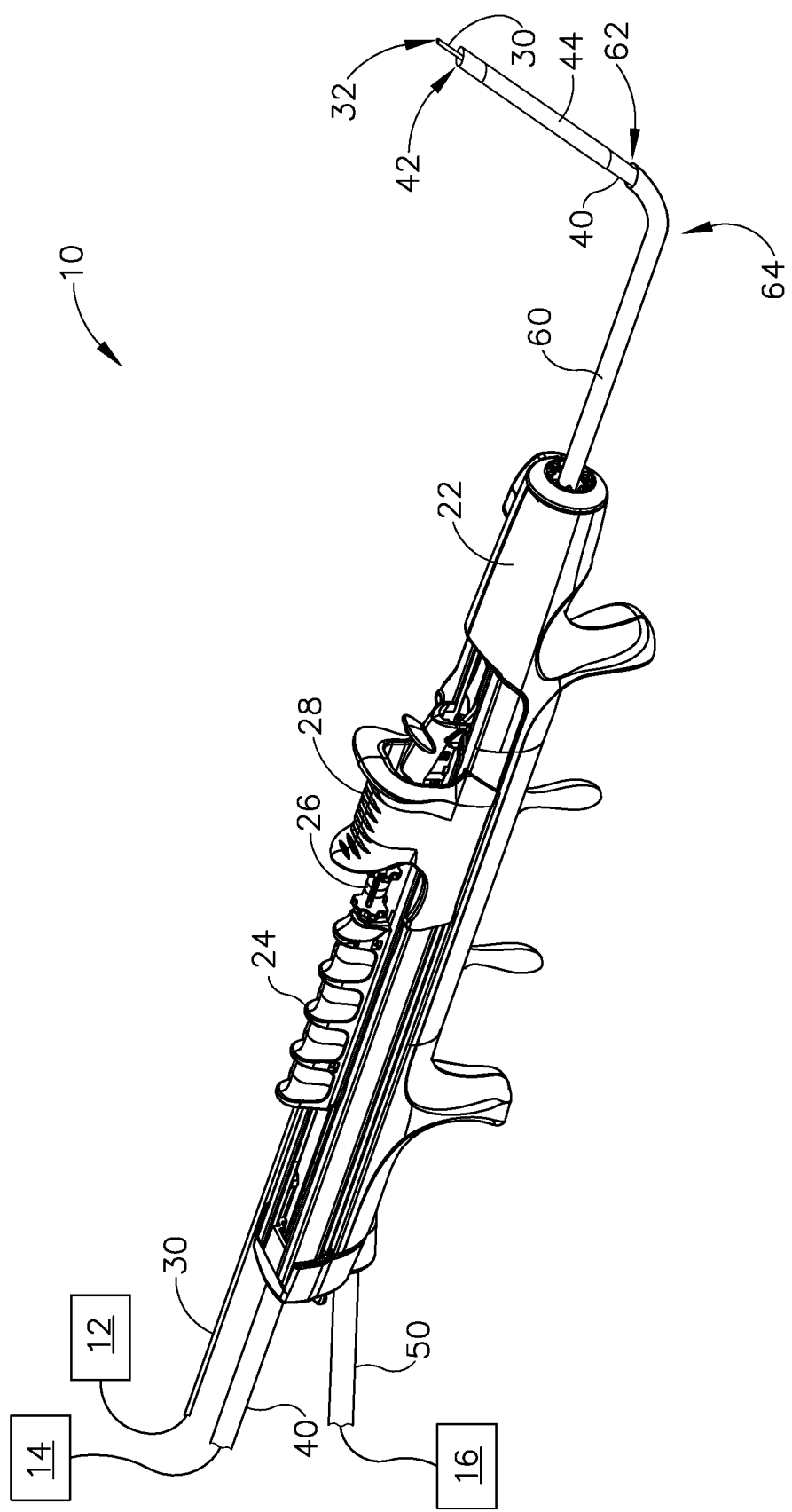
FIG. 1C depicts a perspective view of the dilation instrument assembly of FIG. 1A, with the guidewire in a distal position, with the dilation catheter in a distal position, and with a dilator of the dilation catheter in a non-dilated state.

Dilation instrument (30) further comprises a dilation catheter (40), which is coaxially disposed in guide catheter (60). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (62) of guide catheter (60). As can also be seen in FIG. 1C, a distal portion of guidewire (30) protrudes distally from the open distal end of dilation catheter (40) when guidewire (30) and dilation catheter are both in distal positions.

Figure 1D:
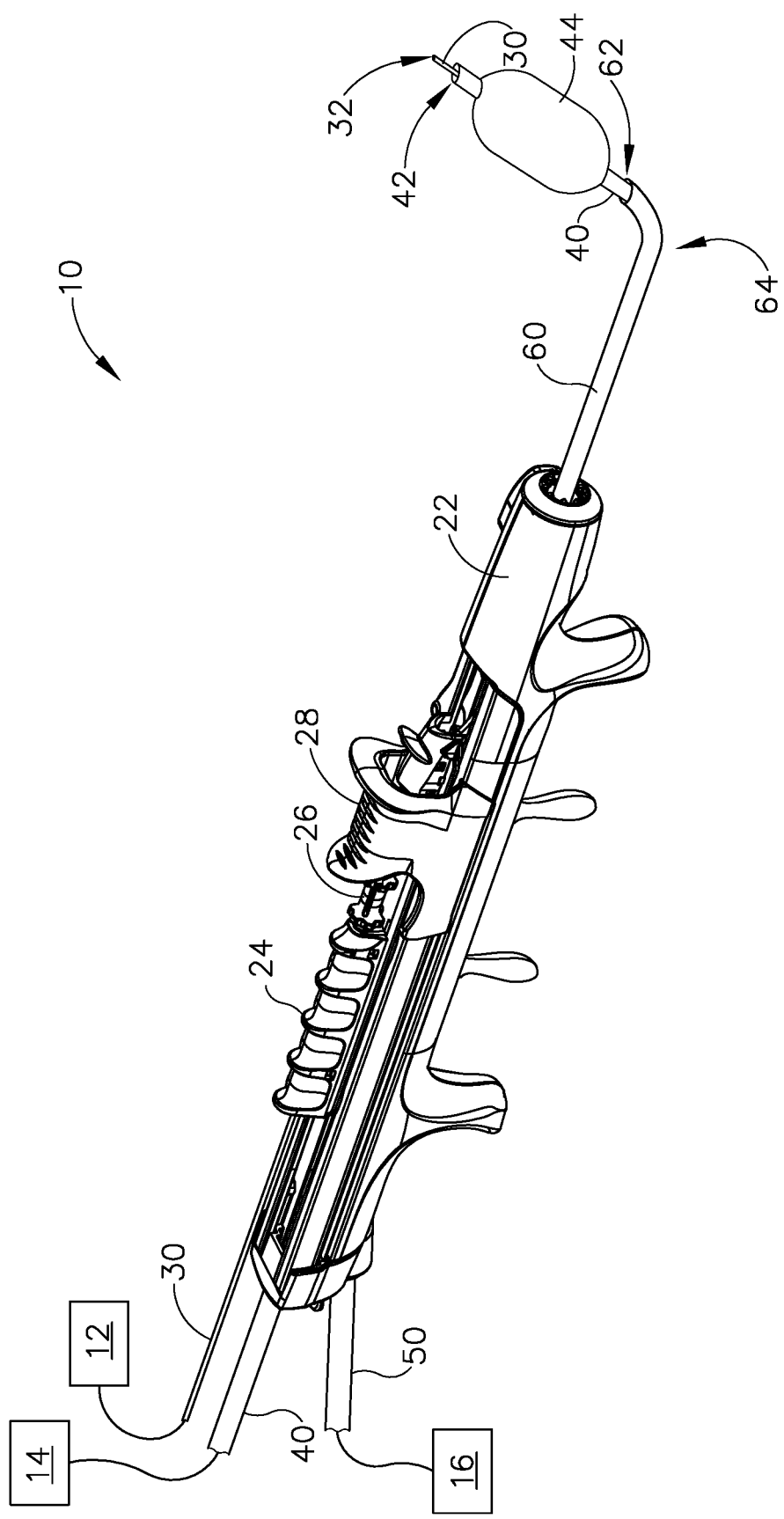
FIG. 1D depicts a perspective view of the dilation instrument assembly of FIG. 1A, with the guidewire in a distal position, with the dilation catheter in the distal position, and with a dilator of the dilation catheter in a dilated state.

Dilation catheter (40) of the present example comprises a non-extensible balloon (44) located just proximal to open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In some versions, inflation source (14) comprises a manually actuated source of pressurized fluid. In some such versions, the manually actuated source of pressurized fluid is configured and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein. Other suitable configurations that may be used to provide a source of pressurized fluid will be apparent to those of ordinary skill in the art in view of the teachings herein.

While not shown, it should be understood that dilation catheter (40) may include at least two separate lumens that are in fluid isolation relative to each other. One lumen may provide a path for fluid communication between balloon (44) and inflation source (14). The other lumen may provide a path to slidably receive guidewire (30).

While dilation catheter (40) of the present example is configured to transition between a non-dilated state and a dilated state based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar to the Relieva Ultirra™ Sinus Balloon Catheter by Acclarent, Inc. of Irvine, Calif. In some other versions, dilator catheter (40) is configured and operable similar to the Relieva Solo Pro™ Sinus Balloon Catheter by Acclarent, Inc. of Irvine, Calif. Other suitable variations of dilation catheter (40) will be apparent to those of ordinary skill in the art in view of the teachings herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, Calif. Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, Calif.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein. Of course, irrigation may be provided in the absence of a dilation procedure; and a dilation procedure may be completed without also including irrigation. It should therefore be understood that dilation fluid source (16) and tube (50) are merely optional.

E. Exemplary Variations

In the present example, guidewire (30) is coaxially disposed within dilation catheter (40), which is coaxially disposed within guide catheter (60). In some other versions, guide catheter (60) is omitted from dilation instrument (20). In some such versions, a malleable guide member is used to guide guidewire (30) and dilation catheter (40). In some such versions, guidewire (30) is omitted and dilation catheter (40) is slidably disposed about the exterior of the internal malleable guide member. In some other versions, guidewire (30) is slidably disposed about the exterior of the internal malleable guide member; and dilation catheter (40) is slidably disposed about the exterior of guidewire (30). In still other versions, guidewire (30) is slidably disposed within the interior of the malleable guide member; and dilation catheter (40) is slidably disposed about the exterior of the malleable guide member.

By way of example only, versions of dilation instrument (20) that include a malleable guide member may be constructed and operable in accordance with at least some of the teachings of U.S. Pub. No. 2016/0310714, entitled "Balloon Dilation System with Malleable Internal Guide," published Oct. 27, 2016, issued as U.S. Pat. No. 10,137,285 on Nov. 27, 2018, the disclosure of which is incorporated by reference herein. As another merely illustrative example, versions of dilation instrument (20) that include a malleable guide member may be constructed and operable in accordance with at least some of the teachings of U.S. patent application Ser. No. 14/928,260, entitled "Apparatus for Bending Malleable Guide of Surgical Instrument," filed Oct. 30, 2015, issued as U.S. Pat. No. 10,137,286 on Nov. 27, 2018, the disclosure of which is incorporated by reference herein; and/or U.S. Pub. No. 2012/0071857, entitled "Methods and Apparatus for Treating Disorders of the Sinuses," published Mar. 22, 2012, now abandoned, the disclosure of which is incorporated by reference herein.

It should be understood that the variations of dilation instrument (20) described below in the context of an IGS system may be incorporated into versions of dilation instrument (20) having a malleable guide just like the variations of dilation instrument (20) described below in the context of an IGS system may be incorporated into versions of dilation instrument (20) having a rigid guide catheter (60).

Various examples below describe the use of an IGS system to provide navigation of instruments within a patient. In particular, various examples below describe how dilation instrument assembly (10) may be modified to incorporate IGS system features. However, it should also be understood that dilation instrument assembly (10) may be used in conjunction with conventional image guidance instruments, in addition to being used with IGS system components. For instance, dilation instrument assembly (10) may be used in conjunction with an endoscope, at least to provide initial positioning of guide catheter (60) in a patient. By way of example only, such an endoscope may be configured in accordance with at least some of the teachings of U.S. Pub. No. 2010/0030031, now abandoned, the disclosure of which is incorporated by reference herein. Other suitable kinds of endoscopes that may be used with the various versions of dilation instrument assembly (10) described herein will be apparent to those of ordinary skill in the art.

Other exemplary dilation catheter systems that may be used include the systems described in U.S. Pat. Nos. 8,777, 926 and 9,095,646, the disclosures of which are incorporated by reference herein; and the RELIEVA ULTIRRA® Sinus Balloon Catheter system by Acclarent, Inc. of Irvine, Calif.

II. Exemplary Image Guided Surgery Navigation System

Figure 2:
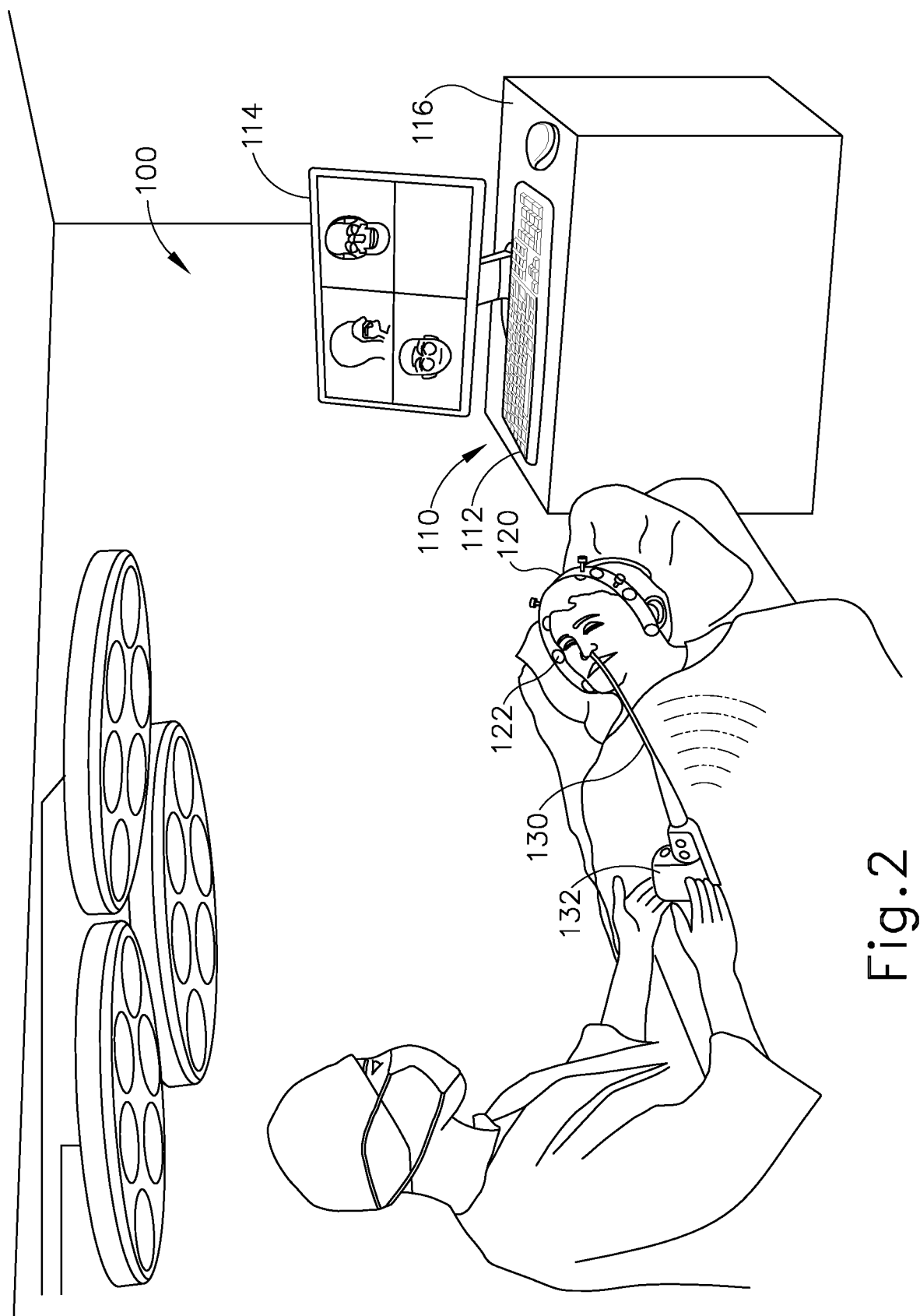
FIG. 2 depicts a schematic view of an exemplary sinus surgery navigation system.

FIG. 2 shows an exemplary IGS navigation system (100) whereby an ENT procedure may be performed using IGS. In some instances, IGS navigation system (100) is used during a procedure where dilation instrument assembly (10) that may be used to dilate the ostium of a paranasal sinus; or to dilate some other anatomical passageway (e.g., within the ear, nose, or throat, etc.). However, it should be understood that IGS navigation system (100) may be readily used in various other kinds of procedures.

In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (100) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

Figure 3:
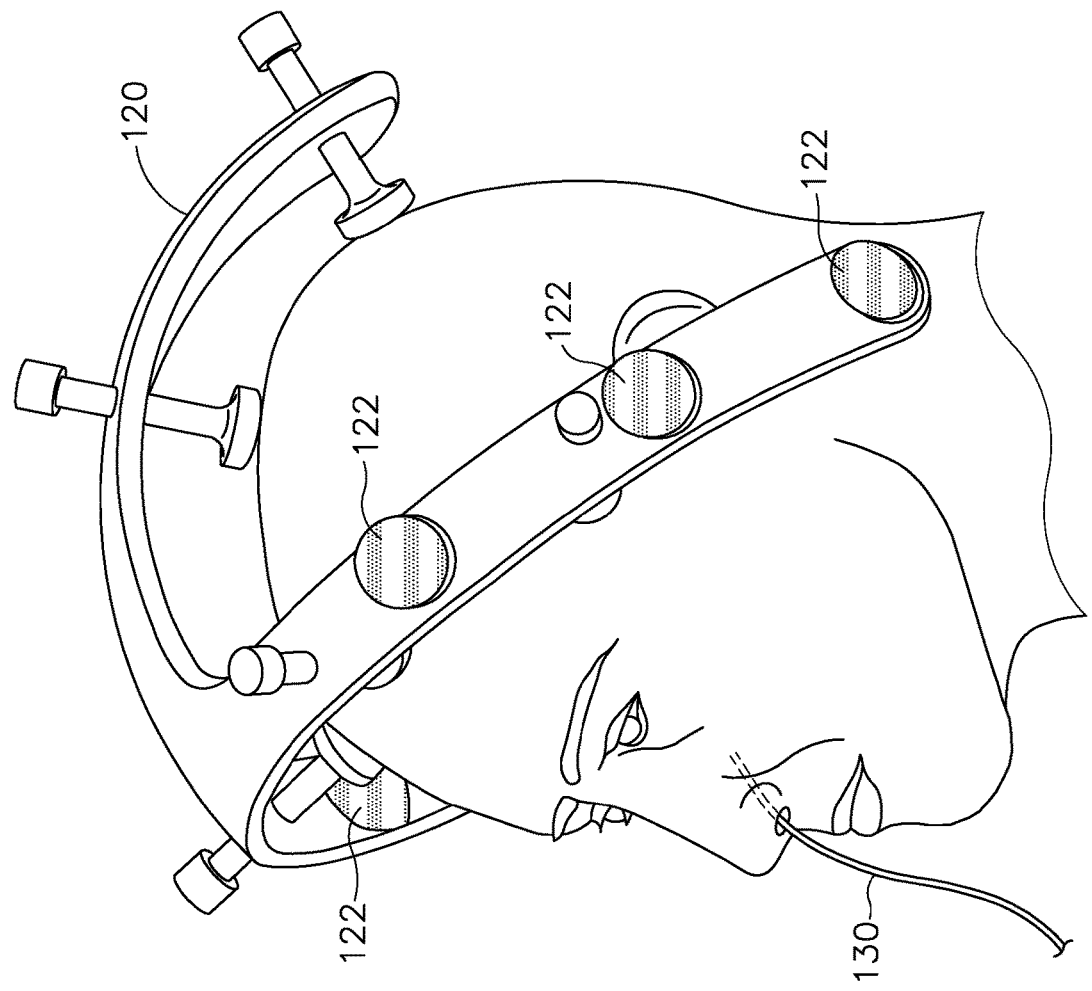
FIG. 3 depicts a perspective view of the head of a patient, with components of the navigation system of FIG. 2.

IGS navigation system (100) of the present example comprises a set of magnetic field generators (122). Before a surgical procedure begins, field generators (122) are fixed to the head of the patient. As best seen in FIG. 3, field generators (122) are incorporated into a frame (120), which is clamped to the head of the patient. While field generators (122) are secured to the head of the patient in this example, it should be understood that field generators (122) may instead be positioned at various other suitable locations and on various other suitable structures. By way of example only, field generators (122) may be mounted on an independent structure that is fixed to a table or chair on which the patient is positioned, on a floor-mounted stand that has been locked in position relative to the head of the patient, and/or at any other suitable location(s) and/or on any other suitable structure(s).

Field generators (122) are operable to generate an electromagnetic field around the head of the patient. In particular, field generators (122) are operated so as to transmit alternating magnetic fields of different frequencies into a region in proximity to frame (120). Field generators (122) thereby enable tracking of the position of a navigation guidewire (130) that is inserted into a nasal sinus of the patient and in other locations within the patient's head. Various suitable components that may be used to form and drive field generators (122) will be apparent to those of ordinary skill in the art in view of the teachings herein.

Navigation guidewire (130) may be used as a substitute for guidewire (30) described above, and may include a sensor (not shown) that is responsive to movement within the fields generated by field generators (122). In particular, signals generated by the sensor of navigation guidewire (130) may be processed by processor (110) to determine the three-dimensional location of navigation guidewire (130) within the patient. Various suitable forms that the sensor may take will be apparent to those of ordinary skill in the art in view of the teachings herein, particularly in view of several of the references that are cited herein in the context of IGS navigation system (100). It should be understood that, when used as a substitute for guidewire (30) in dilation instrument assembly (10), navigation guidewire (130) may facilitate navigation of instrumentation of dilation instrument assembly (10) within the patient during performance of a procedure to dilate the ostium of a paranasal sinus; or to dilate some other anatomical passageway (e.g., within the ear, nose, or throat, etc.). It should also be understood that other components of dilation instrument assembly (10) may incorporate a sensor like the sensor of navigation guidewire (130), including but not limited to the exemplary alternative dilation catheter (200) described below.

IGS navigation system (100) of the present example further comprises a processor (110), which controls field generators (122) and other elements of IGS navigation system (100). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Console (116) also connects to other elements of system (100). For instance, as shown in FIG. 2 a coupling unit (132) is secured to the proximal end of navigation guidewire (130). Coupling unit (132) of this example is configured to provide wireless communication of data and other signals between console (116) and navigation guidewire (130). In some versions, coupling unit (132) simply communicates data or other signals from navigation guidewire (130) to console (116) uni-directionally, without also communicating data or other signals from console (116). In some other versions, coupling unit (132) provides bidirectional communication of data or other signals between navigation guidewire (130) to console (116). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Processor (110) uses software stored in a memory of processor (110) to calibrate and operate system (100). Such operation includes driving field generators (122), processing data from navigational guidewire (130), processing data from operating controls (112), and driving display screen (114). The software may be downloaded to processor (110) in electronic form, over a network, for example, or it may, alternatively or additionally, be provided and/or stored on non-transitory tangible media, such as magnetic, optical, or electronic memory.

Processor (110) is further operable to provide video in real time via display screen (114), showing the position of the distal end of navigational guidewire (130) in relation to a video camera image of the patient's head, a CT scan image of the patient's head, and/or a computer generated three-dimensional model of the anatomy within and adjacent to the patient's nasal cavity. Display screen (114) may display such images simultaneously and/or superimposed on each other. Moreover, display screen (114) may display such images during the surgical procedure. Such displayed images may also include graphical representations of instruments that are inserted in the patient's head, such as navigational guidewire (130), such that the operator may view the virtual rendering of the instrument at its actual location in real time. Such graphical representations may actually look like the instrument or may be a much simpler representation such as a dot, crosshairs, etc. By way of example only, display screen (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head.

In the present example, navigational guidewire (130) includes one or more coils at the distal end of navigational guidewire (130). Such a coil serves as a sensor as referred to above. When such a coil is positioned within an electromagnetic field generated by field generators (122), movement of the coil within that magnetic field may generate electrical current in the coil, and this electrical current may be communicated along the electrical conduit(s) in navigational guidewire (130) and further to processor (110) via coupling unit (132). This phenomenon may enable IGS navigation system (00) to determine the location of the distal end of navigational guidewire (130) within a three-dimensional space as will be described in greater detail below. In particular, processor (110) executes an algorithm to calculate location coordinates of the distal end of navigational guidewire (130) from the position related signals of the coil(s) in navigational guidewire (130).

In some instances, navigational guidewire (130) is used to generate a three-dimensional model of the anatomy within and adjacent to the patient's nasal cavity; in addition to being used to provide navigation for dilation catheter system (100) within the patient's nasal cavity. Alternatively, any other suitable device may be used to generate a three-dimensional model of the anatomy within and adjacent to the patient's nasal cavity before navigational guidewire (130) is used to provide navigation for dilation catheter system (100) within the patient's nasal cavity. By way of example only, a model of this anatomy may be generated in accordance with at least some of the teachings of U.S. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (116). Console (116) may thus render images of at least a portion of the model via display screen (114) and further render real-time video images of the position of navigational guidewire (130) in relation to the model via display screen (114).

III. Exemplary Support Assembly for Navigation System Components

Some medical procedures, including but not limited to medical procedures that are performed in the ear, nose, or throat of a patient (referred to herein as "ENT procedures"), may be performed while the patient is supported by a chair. As shown in FIGS. 2-3, when an ENT procedure is performed with the assistance of an IGS navigation system (100), it may be necessary to position an array of field generators (122) around the patient's head. In the example described above, field generators (122) are mounted to a frame (120), which is mounted to the patient's head. It may be desirable to instead position field generators (122) on a support structure that is not mounted to the patient's head. For instance, when the patient is seated in a chair, it may be desirable to have the field generators (122) supported by the structure of the chair rather than being supported by the patient's head.

Conventional medical procedure chairs, including those designed particularly for use in ENT procedures, may include several metallic components in the headrest of the chair. While such headrests may provide adequate structural support for field generators (122), metallic components in such headrests (and/or elsewhere within the chair) may interfere with the functioning or accuracy of IGS navigation system (100) if the metallic components are too close to field generators (122). It may therefore be desirable to rely on the chair to structurally support field generators (122) while avoiding the risk of metallic features of the chair compromising the functioning or accuracy of IGS navigation system (100). Moreover, it may be desirable to provide a field generator (122) support assembly that may be readily retrofitted to a conventional medical procedure chair, such that a consumer need not purchase an entire new chair in order to obtain the support functionality described above. In versions where the support assembly may be retrofitted to a conventional medical procedure chair, it may be desirable to enable an operator to accomplish such retrofitting without requiring the use of tools such as screwdrivers, etc.

The following examples relate to support assemblies that may be retrofitted to a conventional medical procedure chair, relying on the chair itself (rather than the patient's head) to structurally support IGS navigation system (100) components such as field generators (122), without the risk of any metallic components of the chair interfering with the functioning or accuracy of IGS navigation system (100), and without requiring the use of separate tools in order to complete the retrofitting.

Figure 4:
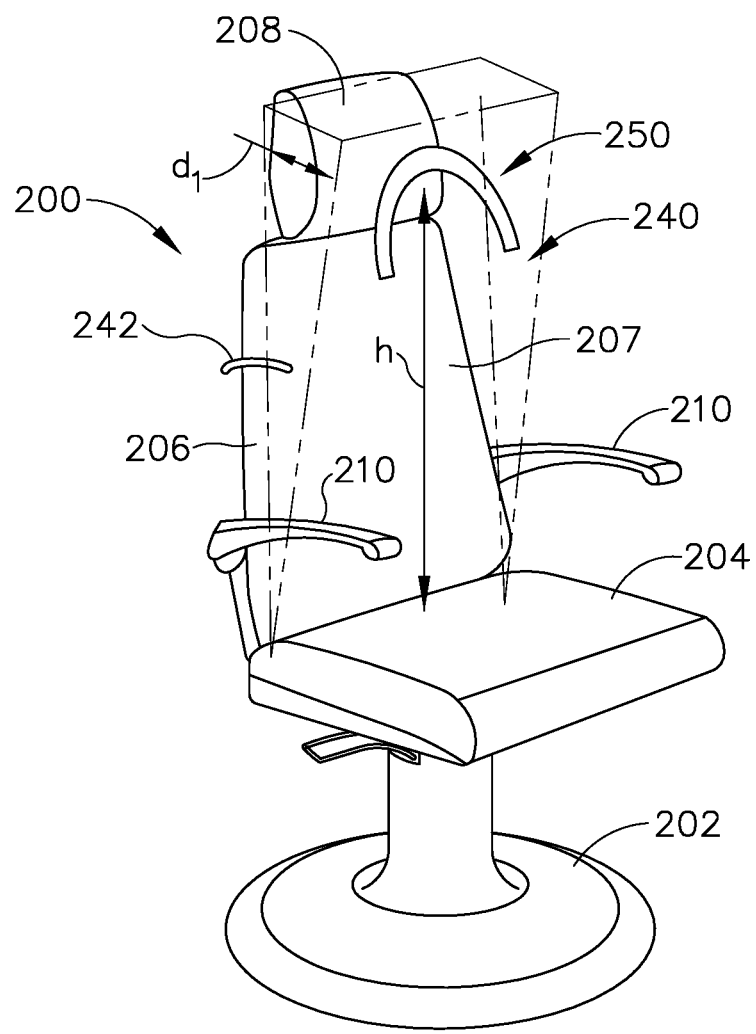
FIG. 4 depicts a perspective view of an exemplary medical procedure chair, with a diagrammatic representation of a navigation component support assembly.

FIG. 4 shows an exemplary ENT procedure chair (200) with a diagrammatically represented support assembly (240) supporting a navigation system component (250). Chair (200) of this example includes a base (202), a bottom support (204), a backrest (206), a headrest (208), and a pair of armrests (210). Backrest (206) includes a front surface (207) and is configured to pivot relative to bottom support (204) to enable positioning of the patient at various recline angles. Support assembly (240) of this example is generally wedge-shaped and is configured to engage front surface (207) of backrest (206), with an upper portion of support assembly (240) extending to a certain distance ($d_1$) from the vertical plane defined by front surface (207). By way of example only, the distance ($d_1$) may be approximately 100 mm. A securing member (242) secures support assembly (240) to backrest (206). Support assembly (240) is configured to support navigation system component (250) at a certain height (h) above bottom support (204). Navigation system component (250) of the present example includes a plurality of field generators like field generators (122) described above; and structures to support such field generators.

A. First Exemplary Support Assembly

Figure 5:
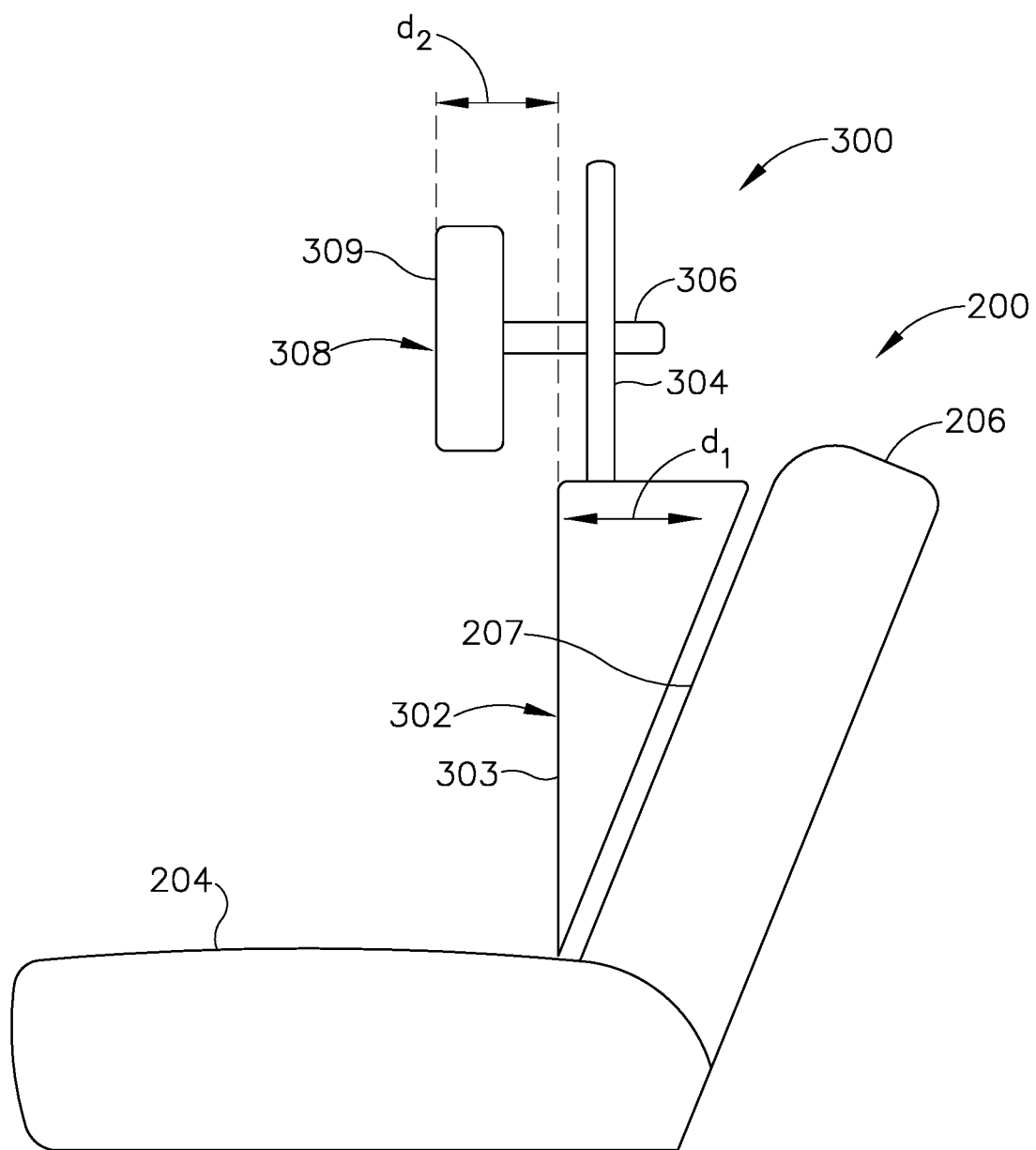
FIG. 5 depicts a side schematic view of the chair of FIG. 4 with another exemplary navigation component support assembly.
Figure 6:
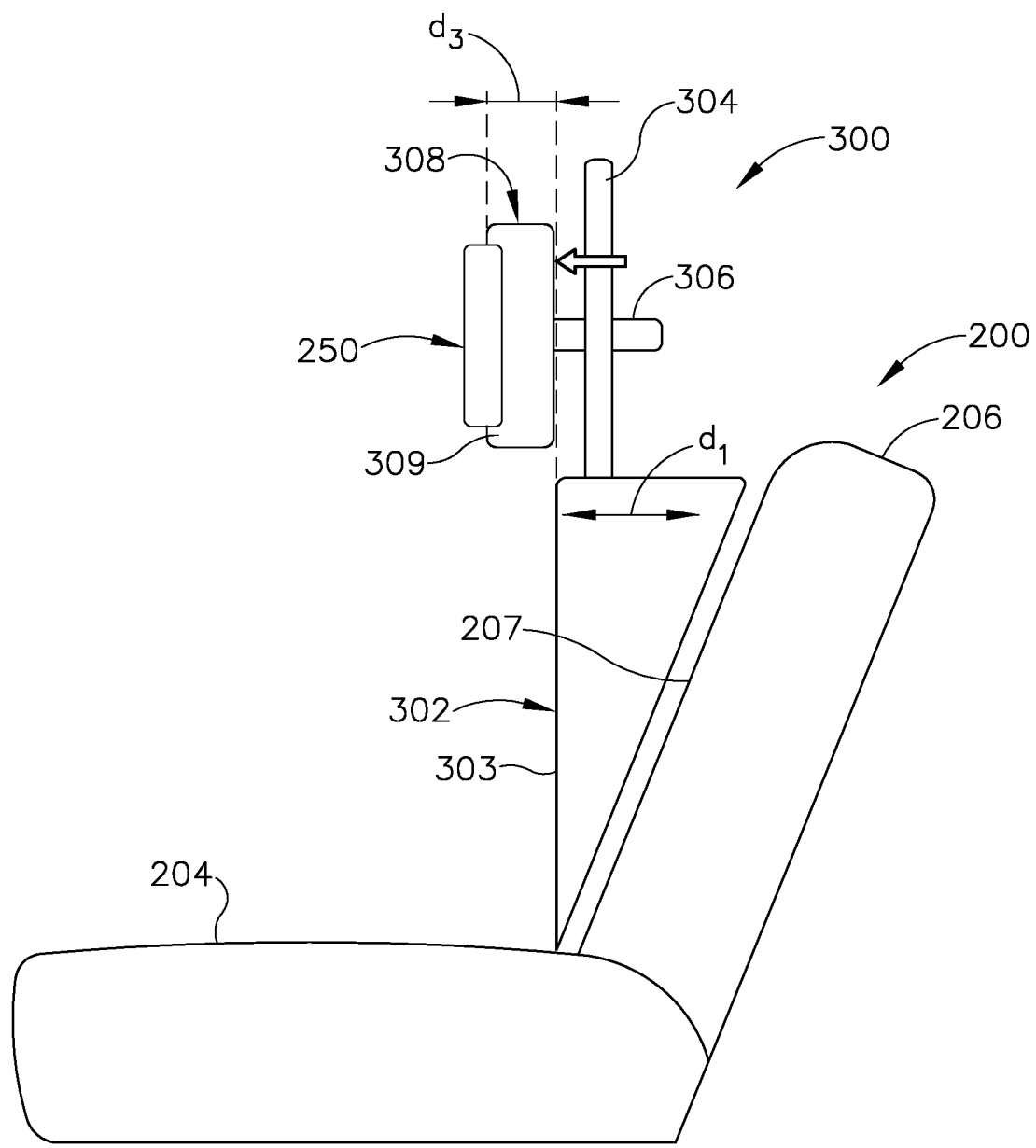
FIG. 6 depicts a side schematic view of the chair of FIG. 4 and the support assembly of FIG. 5, with the navigation component of FIG. 4 secured to the navigation support assembly.

FIGS. 5-6 show an exemplary form that support assembly (240) may take. In particular, FIGS. 5-6 show an exemplary support assembly (300) that includes a wedge-shaped body (302) and resting on front surface (207) of backrest (206). Body (302) includes a front surface (303) upon which a patient's back may rest when the patient is seated on bottom support (204). An upper portion of front surface (303) extends to distance ($d_1$) from the vertical plane defined by front surface (207). A support post (304) extends upwardly from body (302). A headrest support frame (306) is secured to support post (304). In some versions, the vertical position of headrest support frame (306) is adjustable along at least a portion of the height of support post (304). In addition, or in the alternative, headrest support frame (306) may be adjustable laterally (e.g., along the dimension extending left-to-right along the page in FIGS. 5-6) relative to support post (304). A headrest (308) is secured to headrest support frame (306) and is positioned to support a patient's head when the patient is seated on bottom support (204).

In the example shown in FIG. 5, headrest (308) has a front surface (309) that is positioned at a distance ($d_2$) from the vertical plane defined by front surface (303) of body (302). By way of example only, the distance ($d_2$) may be approximately 150 mm. In the example shown in FIG. 6, navigation system component (250) is mounted to headrest (308); and front surface (309) of headrest (308) is positioned at a distance ($d_3$) from the vertical plane defined by front surface (303) of body (302). By way of example only, the distance ($d_3$) may be approximately 50 mm.

B. Second Exemplary Support Assembly

FIGS. 7-15 show another exemplary form that support assembly (240) may take. In particular, FIGS. 7-15 show an exemplary support assembly (500) mounted to another exemplary ENT procedure chair (400). Chair (400) of this example includes a base (402), a bottom support (404), a backrest (406), a pair of armrests (410), and a footrest (412). In this particular example, chair (400) lacks a headrest. In some scenarios, a headrest of chair (400) may be removed to accommodate support assembly (500). Backrest (406) is configured to pivot relative to bottom support (404) in order to achieve various recline angles.

Figure 7:
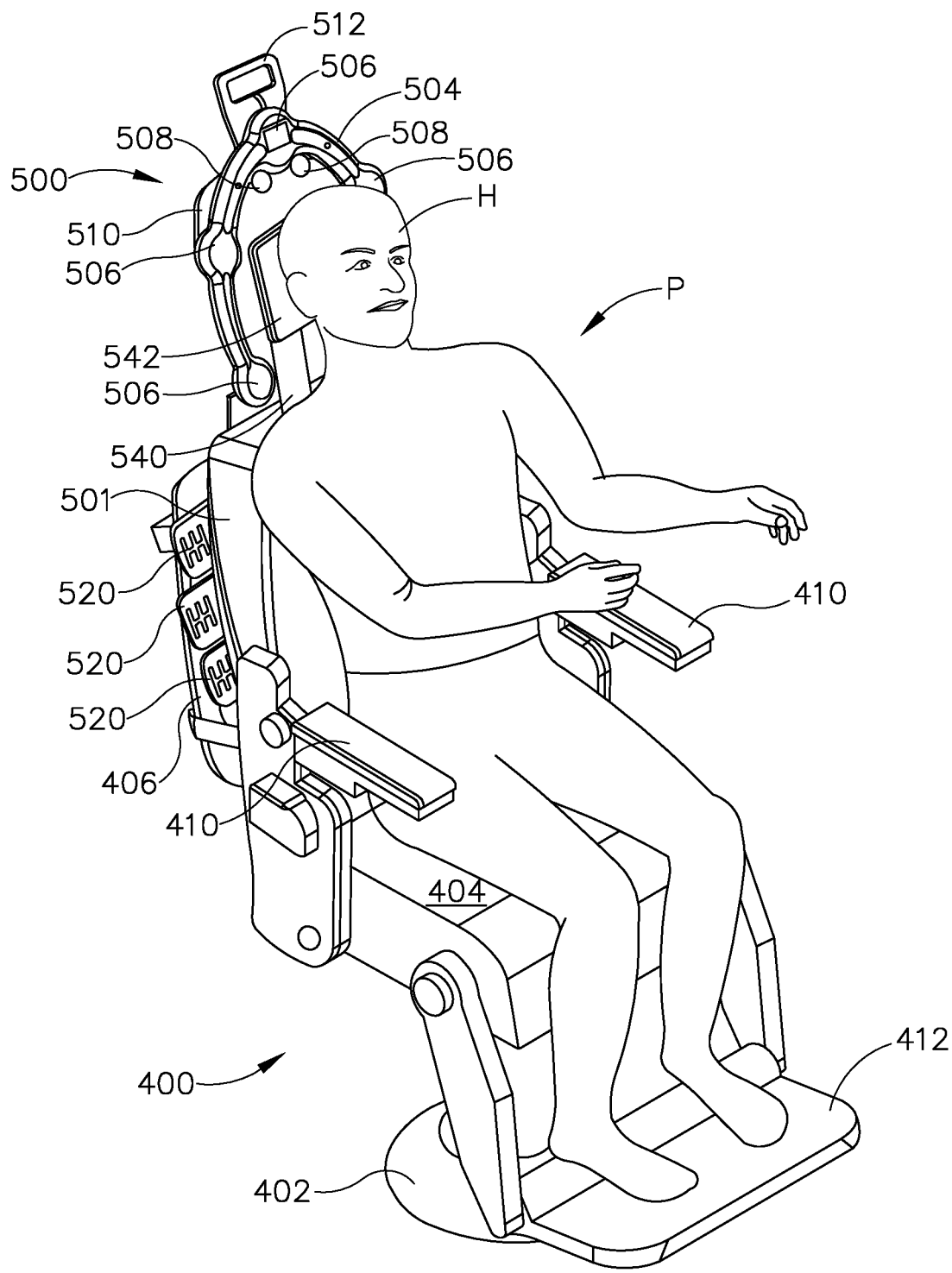
FIG. 7 depicts a front perspective view of another exemplary medical procedure chair, with an exemplary navigation component support assembly secured to the chair, and with a representation of a patient seated in the chair.
Figure 8:
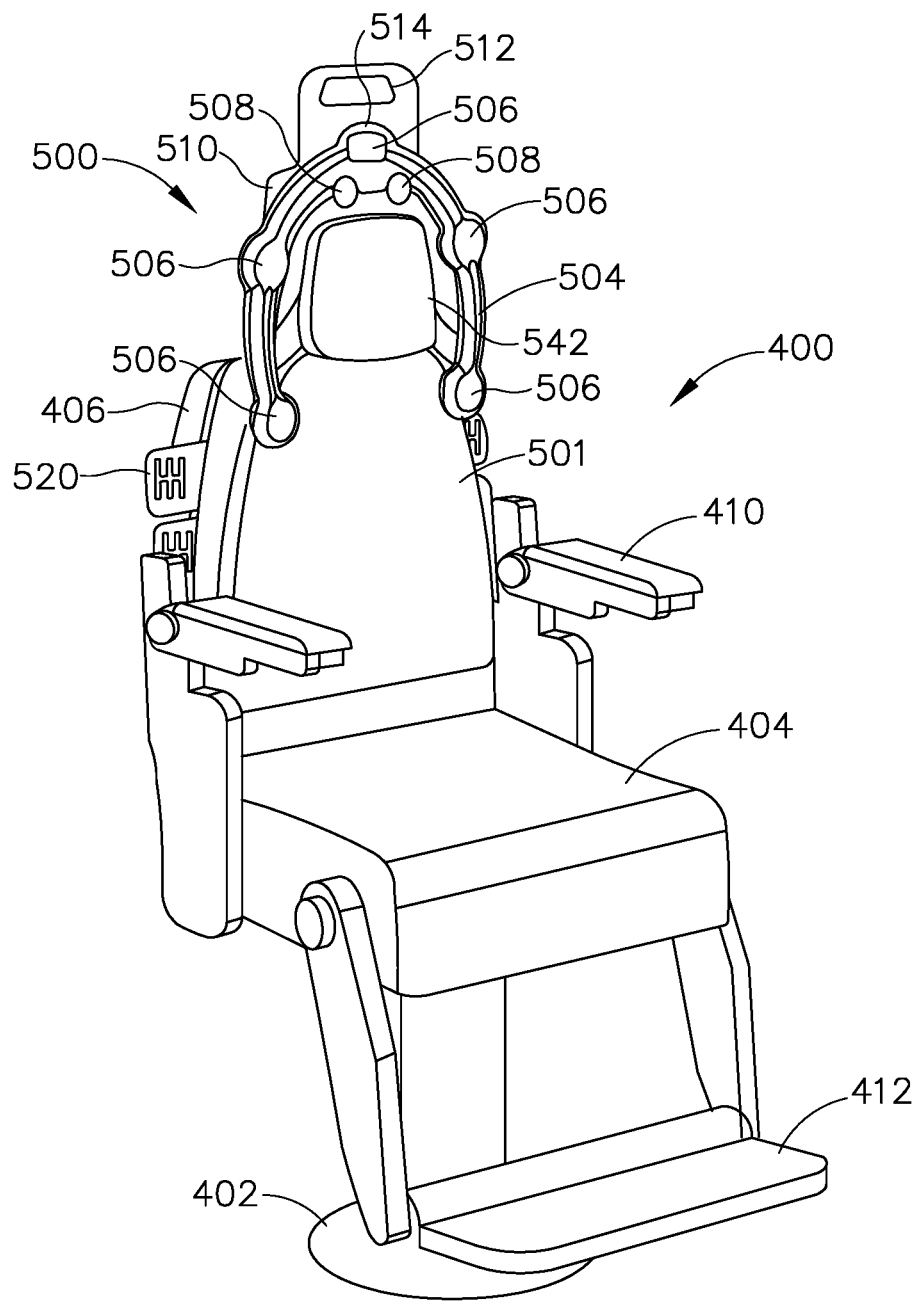
FIG. 8 depicts a front perspective view of the chair and support assembly of FIG. 7.
Figure 9:
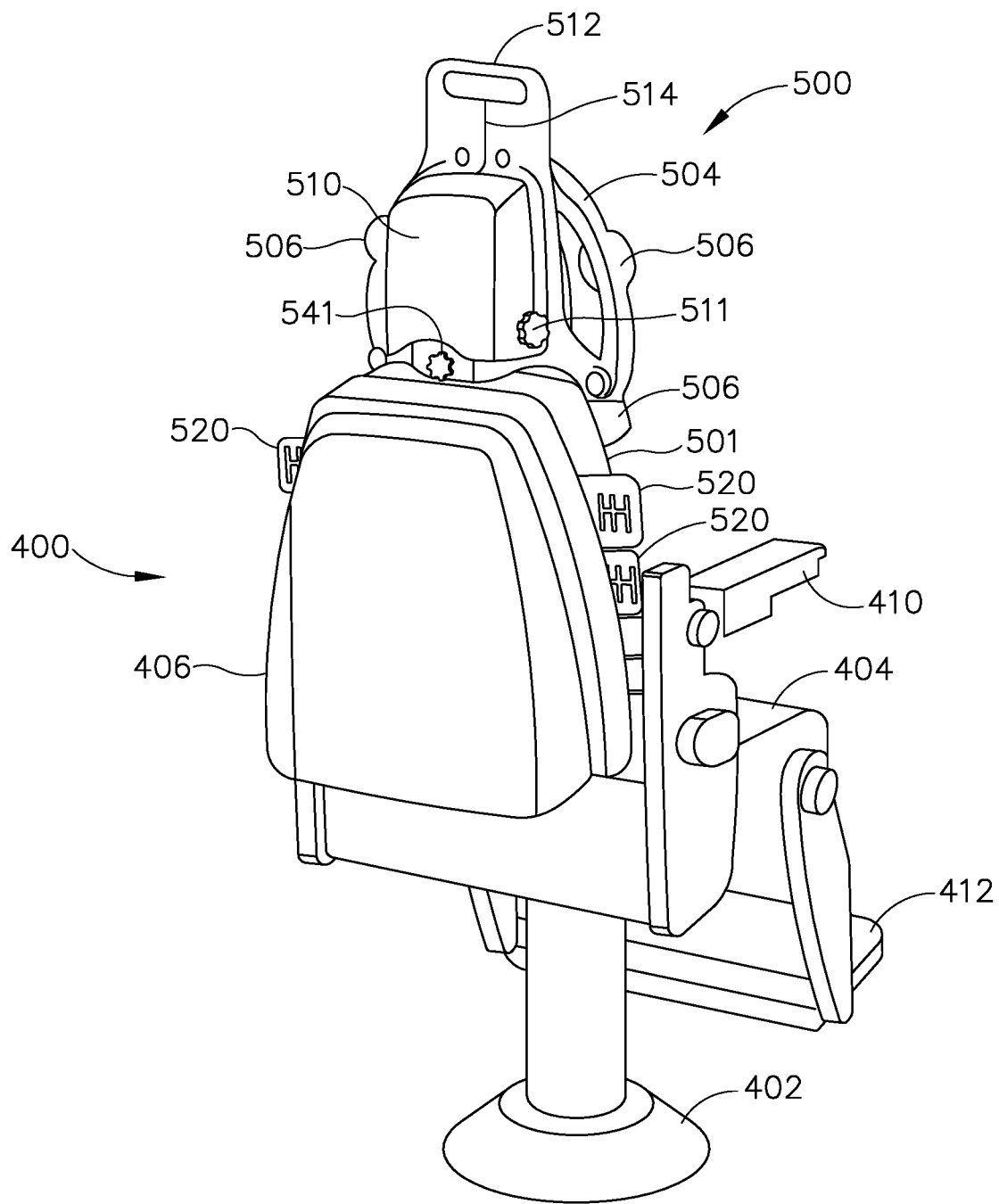
FIG. 9 depicts a rear perspective view of the chair and support assembly of FIG. 7.

Support assembly (500) of this example includes a wedge-shaped body (501) that is configured to rest against a front surface (not shown) of backrest (406). A post (540) extends upwardly from body (501) and supports a housing (510). A frame (504) is secured to the front of housing (510). Frame (504) is generally shaped like a horseshoe in this example and includes a plurality of integral field generators (506). Field generators (506) of this example are configured and operable just like field generators (122) described above. A pair of securing features (508) secure frame (504) to a plate (516) (best seen in FIG. 14) that is secured in housing (510). A headrest (542) is secured to the front of plate (516). As shown in FIG. 7, headrest (542) is configured to support the head (H) of a patient (P) while the patient (P) is seated on bottom support (404). As also shown in FIG. 7, frame (504) is configured to hold field generators (506) in a generally horseshoe-shaped arrangement about the head (H) of the patient (P), without frame (504) contacting the head (H) of the patient (P).

As best seen in FIGS. 9-11 and 14, plate (516) defines a handle (512) with a cable (514) extending therethrough. Cable (514) is in communication with field generators (506) and thereby provides a conduit for communication between field generators (506) and processor (110) of IGS navigation system (100). Handle (512) is configured to be grasped by an operator to position plate (512) (and, hence, frame (504), field generators (506), and headrest (542)) relative to post (540). A knob (541) may be rotated to selectively lock and unlock the vertical position of plate (512) (and, hence, frame (504), field generators (506), and headrest (542)) relative to post (540). By way of example only, the vertical position of plate (512) (and, hence, frame (504), field generators (506), and headrest (542)) relative to post (540) may be adjustable along a range of motion extending through approximately 15 cm or 20 cm.

A pair of knobs (511) may be rotated to selectively lock and unlock the lateral position (i.e., fore and aft) of plate (512) (and, hence, frame (504), field generators (506), and headrest (542)) relative to post (540). By way of example only, knobs (511) may enable the operator to adjust the fore and aft position of plate (512) (and, hence, frame (504), field generators (506), and headrest (542)) such that the rear surface of frame (504) is at least approximately 15 cm from the front surface of body (501). By way of further example only, the fore and aft positon of plate (512) (and, hence, frame (504), field generators (506), and headrest (542)) may be adjustable between an aft-most position where the rear surface of frame (504) is approximately 15 cm from the front surface of backrest (406); and a fore-most position where the rear surface of frame (504) is approximately 25 cm from the front surface of backrest (406).

While chair (400) of the present example lacks an integral headrest, knobs (511, 541) may be positioned such that knobs (511, 541) are still readily accessible even in scenarios where support assembly (500) is used with a chair that still has an integral headrest.

Figure 10:
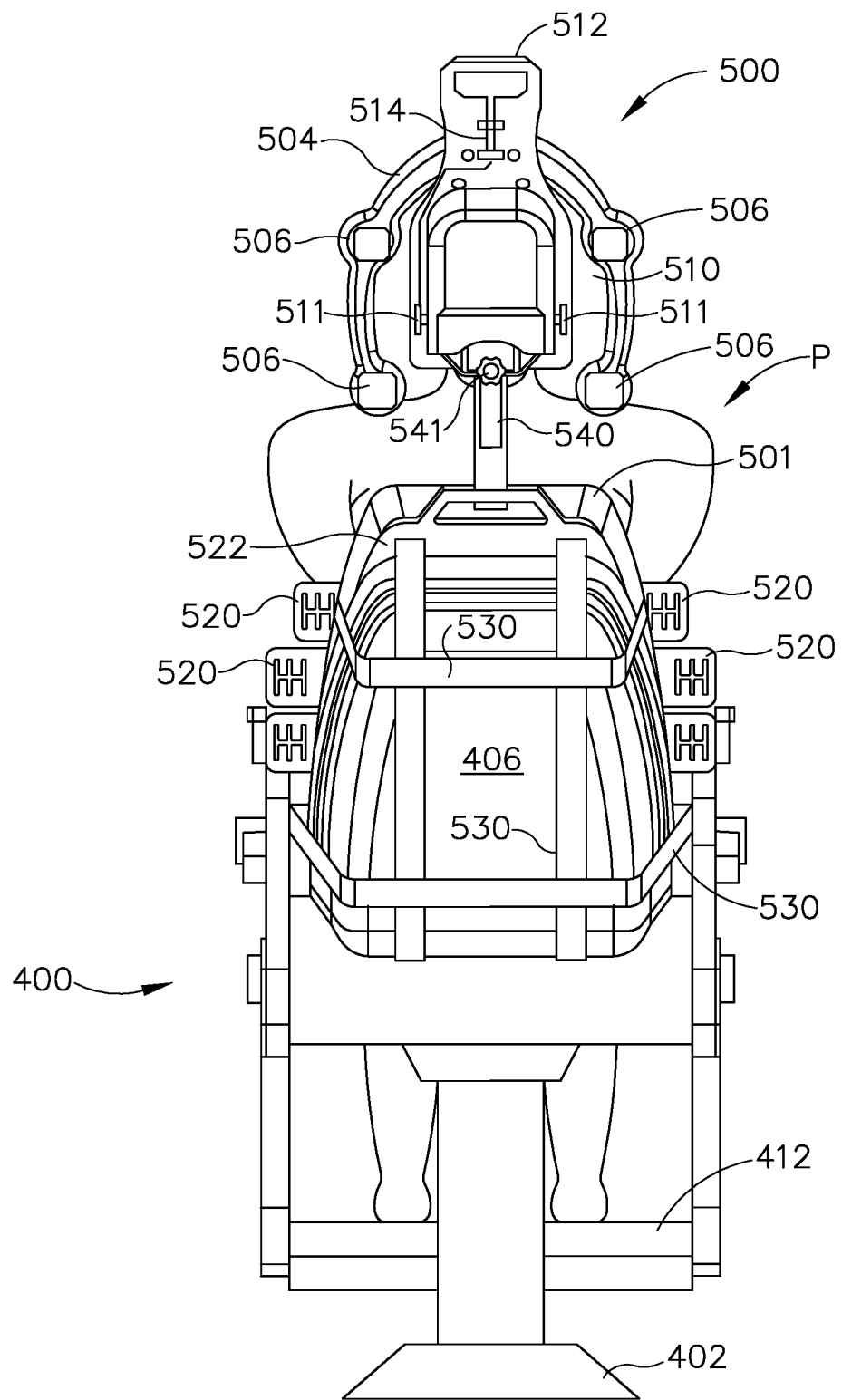
FIG. 10 depicts a rear elevational view of the chair and support assembly of FIG. 7.
Figure 11:
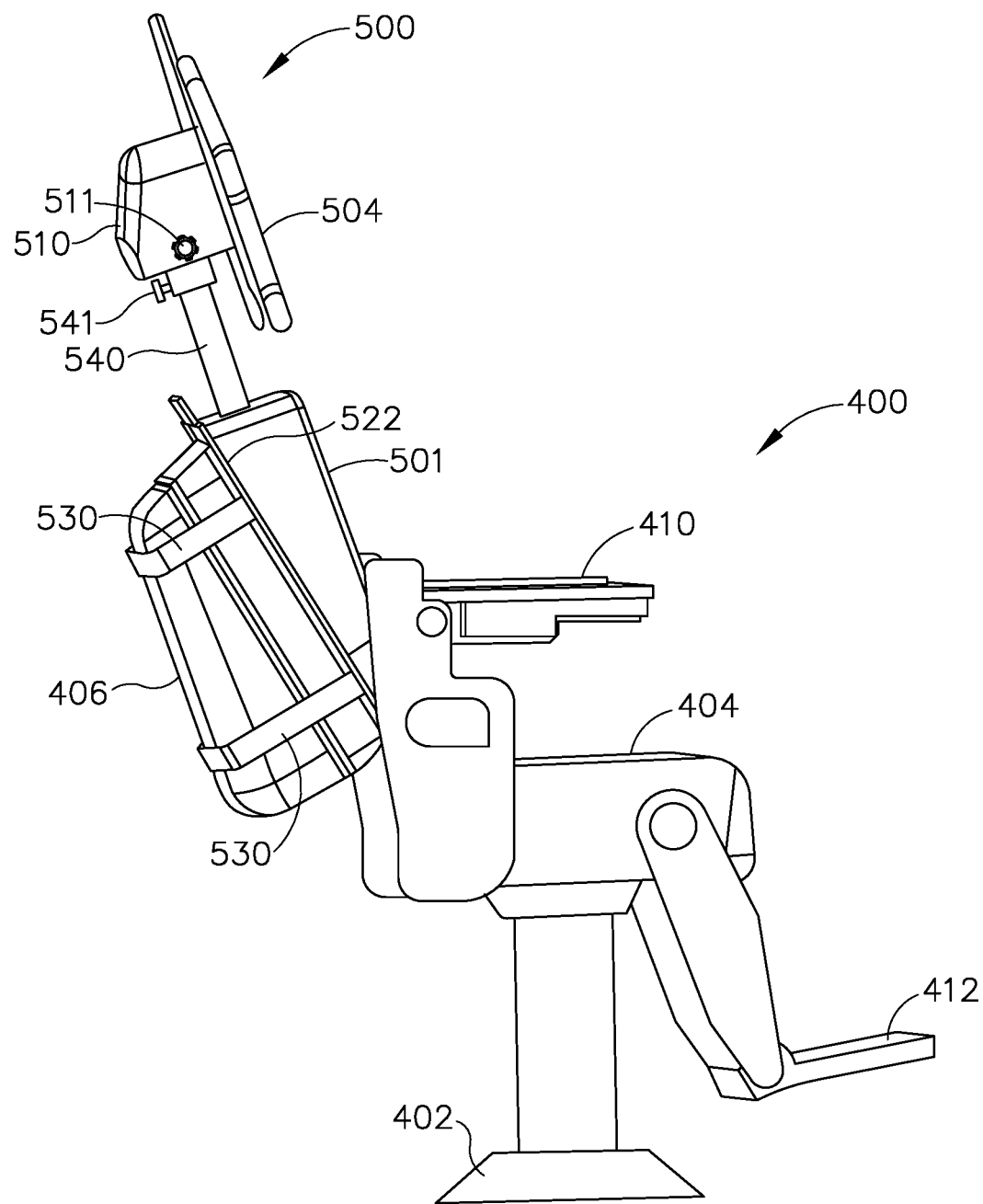
FIG. 11 depicts a side elevational view of the chair and support assembly of FIG. 7.
Figure 12:
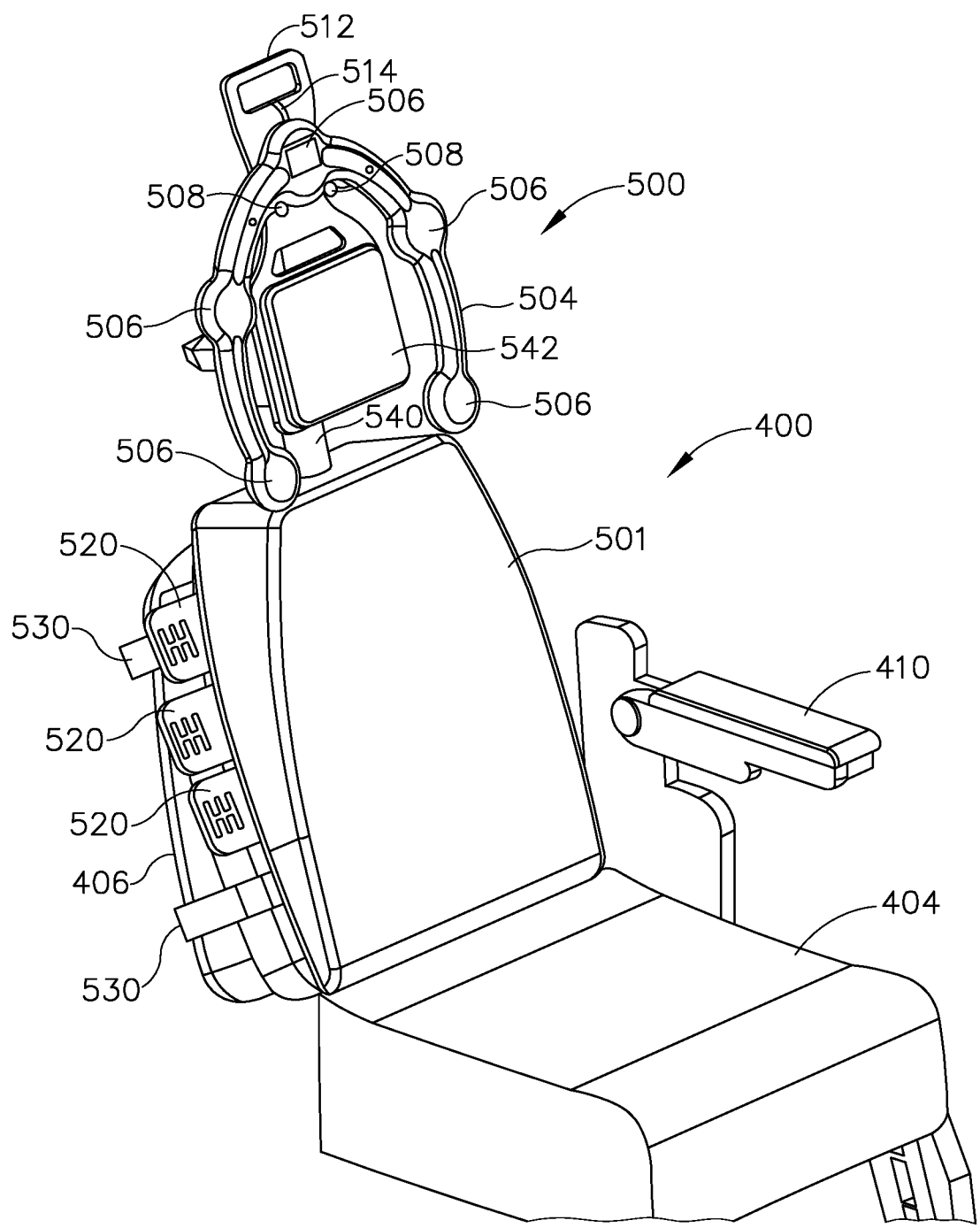
FIG. 12 depicts an enlarged perspective view of the chair and support assembly of FIG. 7, with a portion of the chair omitted.
Figure 13:
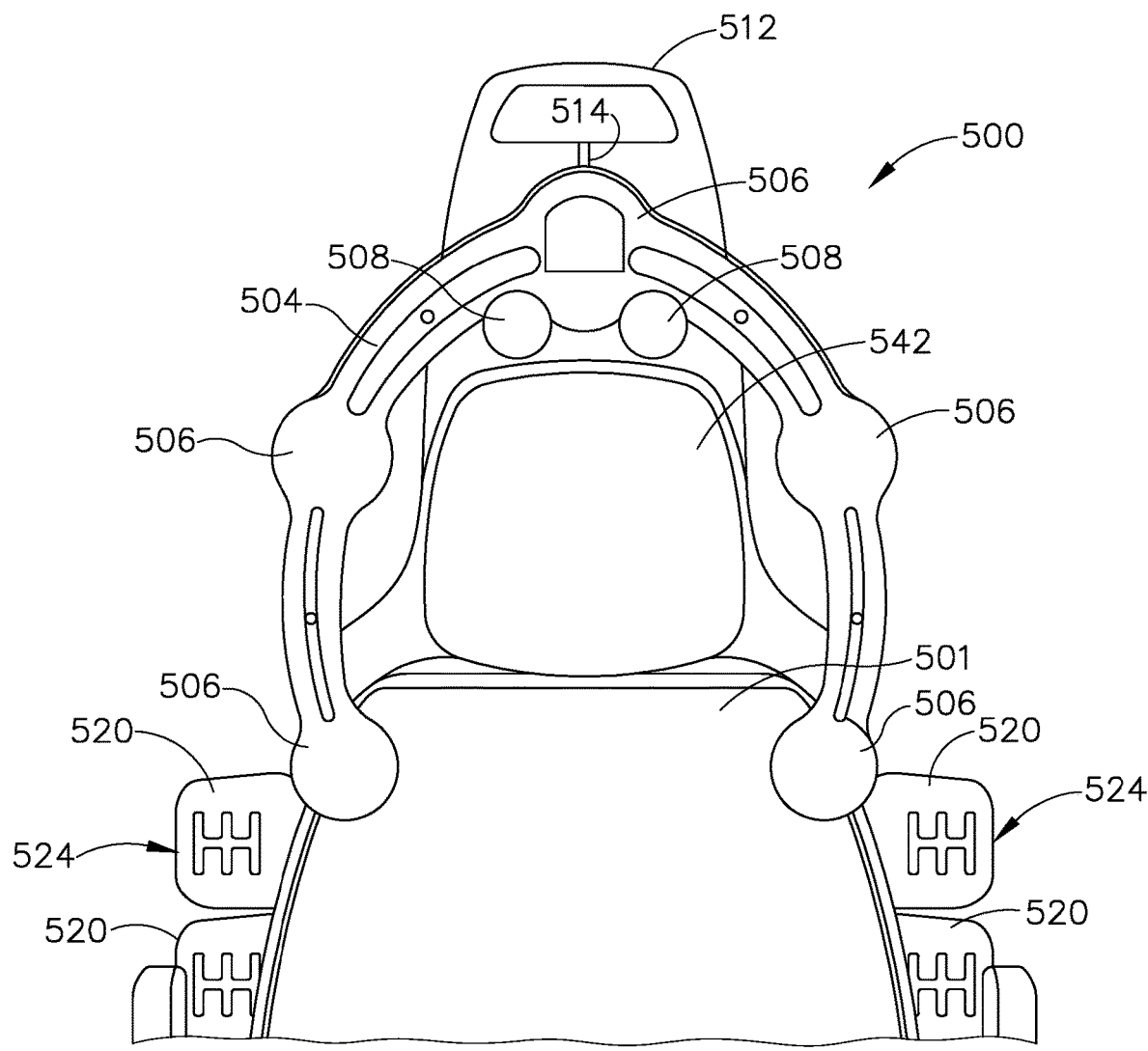
FIG. 13 depicts an enlarged front elevational view of an upper portion of the chair and support assembly of FIG. 7.
Figure 14:
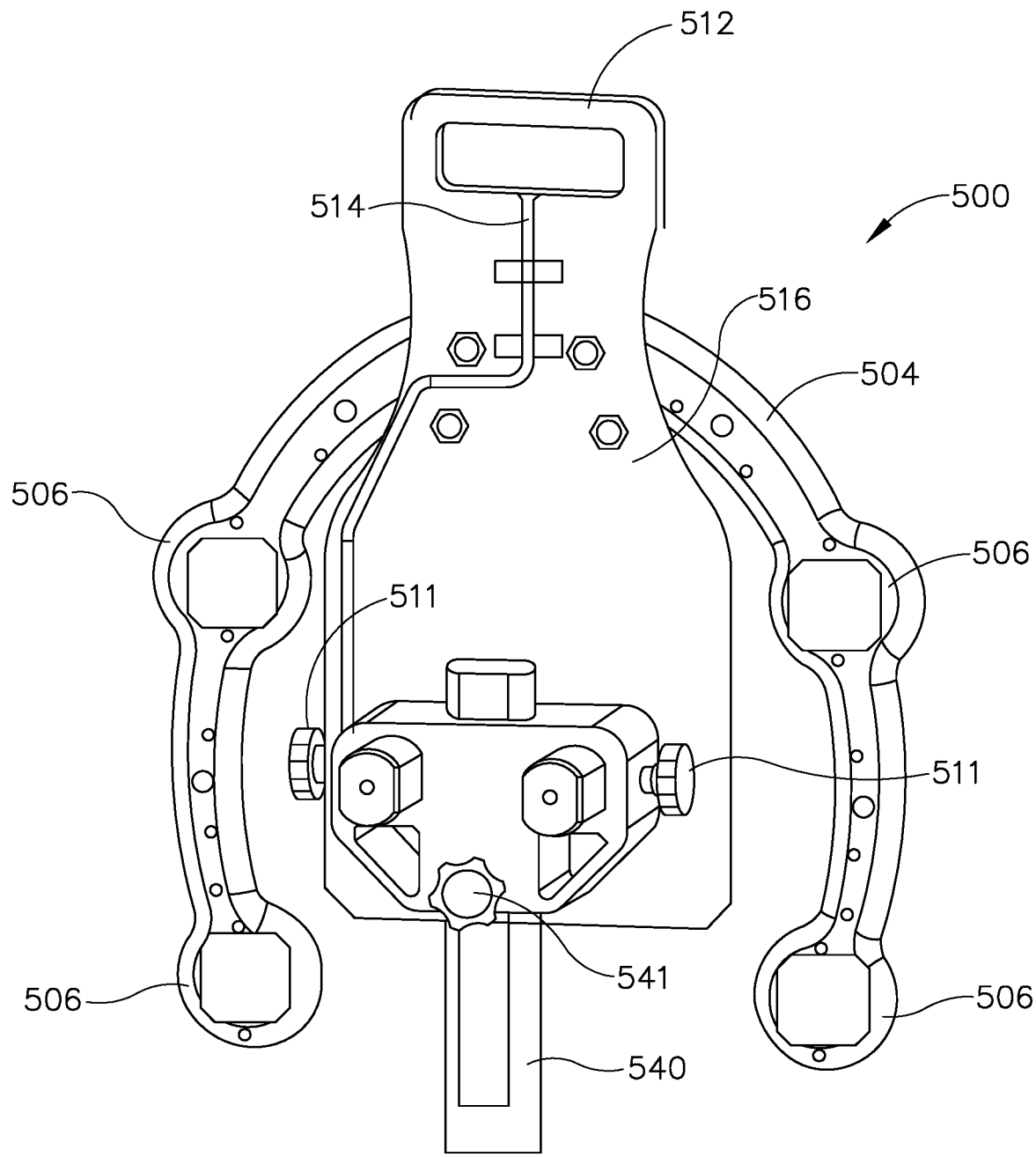
FIG. 14 depicts an enlarged rear perspective view of an upper portion of the support assembly of FIG. 7, with a portion of the support assembly omitted.
Figure 15:
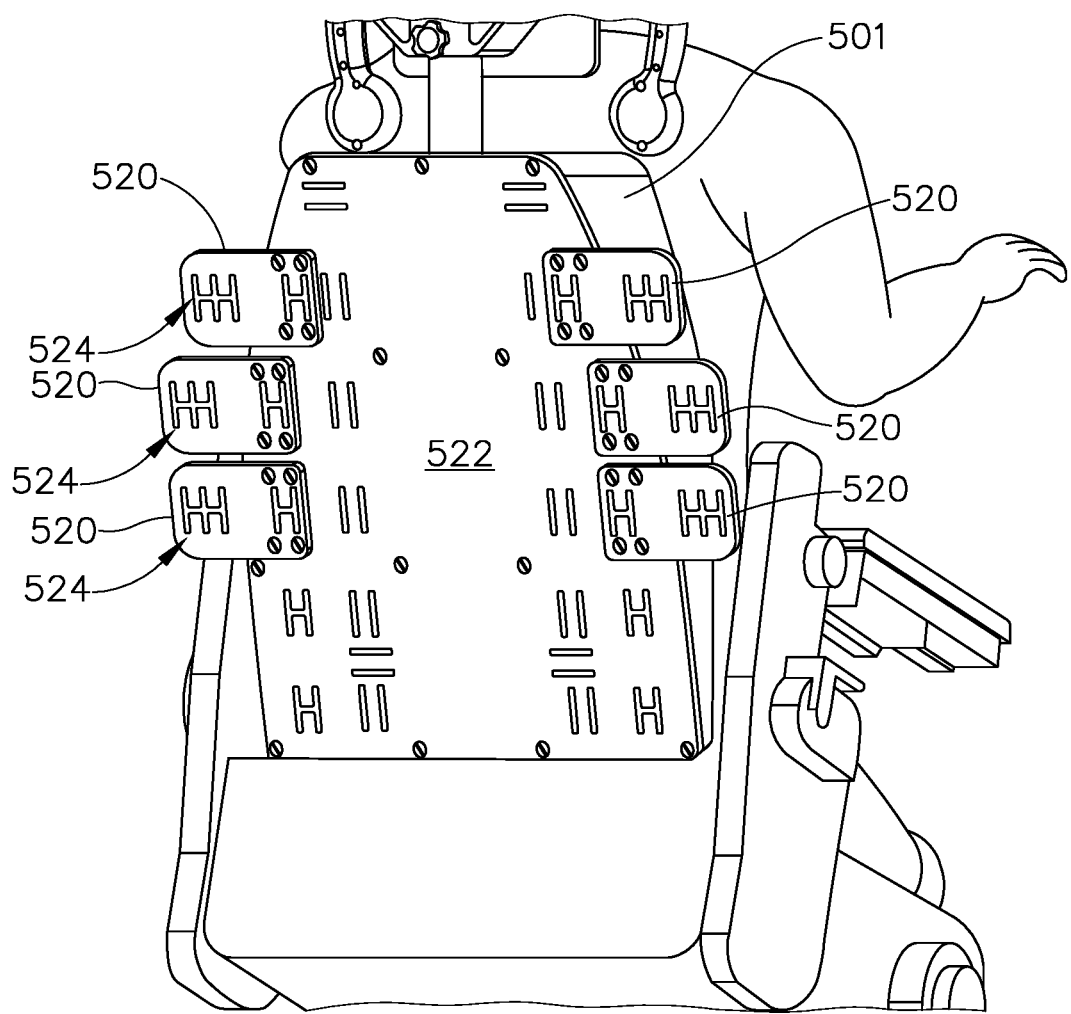
FIG. 15 depicts an enlarged rear perspective view of a lower portion of the support assembly of FIG. 7, with a portion of the chair of FIG. 7 omitted.

Support assembly (500) of the present example further includes a set of mounting tabs (520) extending laterally from a rear plate (522) of body (501). As best seen in FIG. 15, each mounting tab (520) includes a slot set (524) that is configured to receive a strap (530). As best seen in FIGS. 10-12, straps (530) are configured to secure support assembly (500) to backrest (406) of chair (400). Straps (530) may include latches, buckles, and/or any other suitable features that enable the operator to secure straps (530) around the back of backrest (406) and provide tension in straps (530) to thereby firmly secure support assembly (500) to backrest (406). Various features that may be added to straps (530) to enable easy securing of support assembly (500) to backrest (406), and removal of support assembly (500) from backrest (406), will be apparent to those of ordinary skill in the art in view of the teachings herein.

Those of ordinary skill in the art will recognize that the use of straps (530) to secure support assembly (500) to backrest (406) may facilitate securing of support assembly (500) to various kinds of backrests having different widths and thicknesses, such that straps (530) may enhance the ability of support assembly (500) to be retrofitted to different kinds of chairs. Moreover, straps (530) enable the operator to secure support assembly (500) to a chair such as chair (400) without requiring the operator to use separate tools (e.g., wrenches, screwdrivers, etc.). In addition, straps (530) will not damage backrest (406), such that chair (400) will not be damaged by the addition of support assembly (500). This enables chair (400) to be readily used in subsequent procedures after support assembly (500) is removed.

C. Third Exemplary Support Assembly

Figure 16:
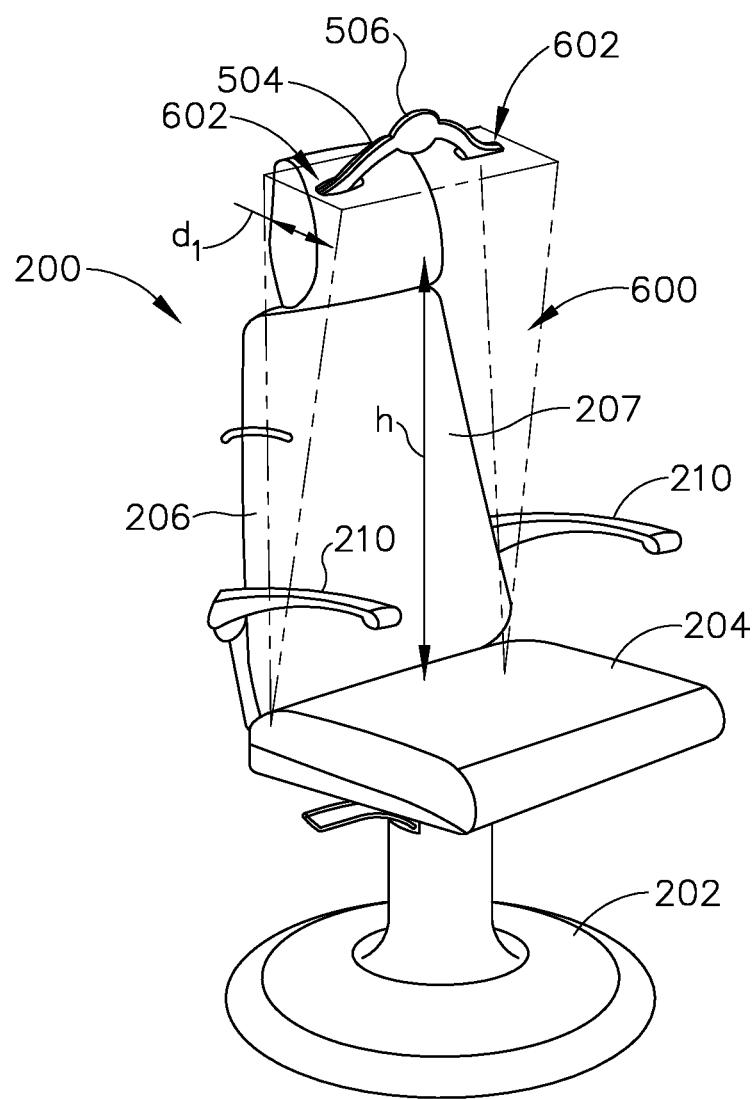
FIG. 16 depicts a perspective view of the chair of FIG. 4, with another exemplary navigation support assembly.
Figure 17:
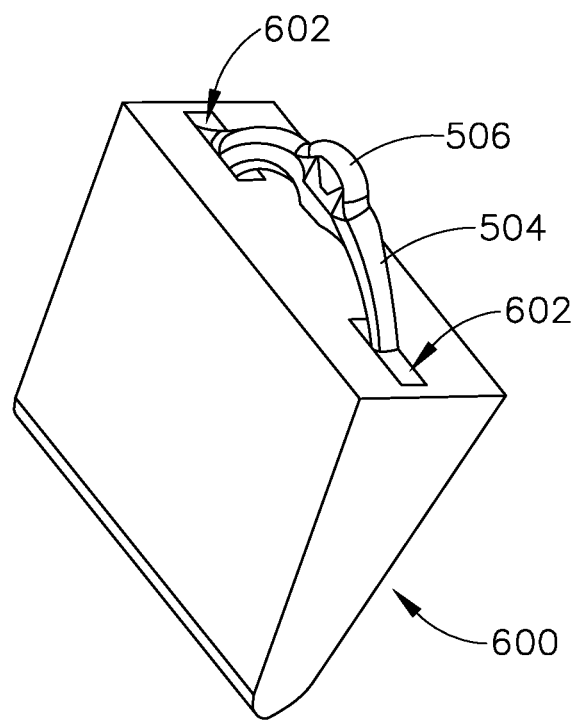
FIG. 17 depicts a perspective view of the navigation support assembly of FIG. 16.
Figure 18:
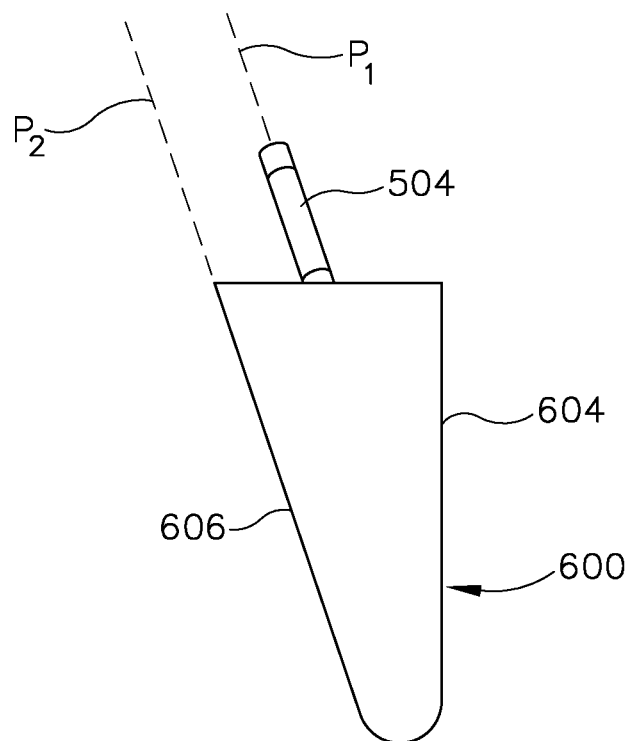
FIG. 18 depicts a side elevational view of the navigation support assembly of FIG. 16.
Figure 19:
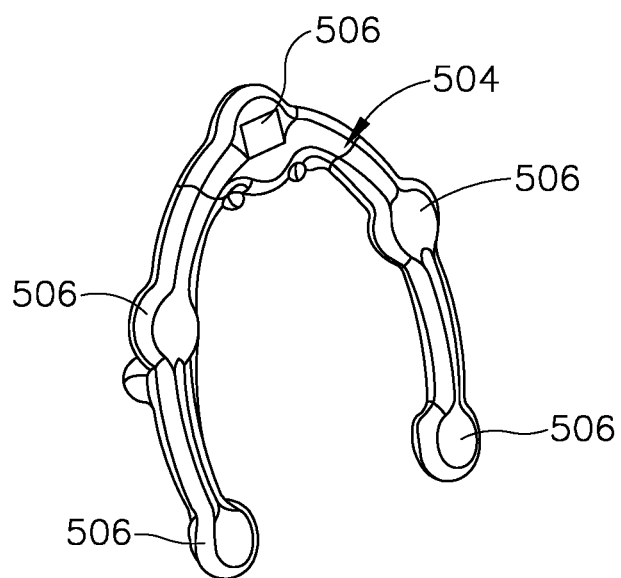
FIG. 19 depicts a perspective view of a frame assembly of the navigation support assembly of FIG. 16.

FIGS. 16-18 show an exemplary alternative support assembly (600) in the form of a simple foam pad that is configured to engage backrest (206) and headrest (208) of a conventional chair (200). As shown, support assembly (600) is wedge-shaped, with a rear surface (604) and a front surface (606). Rear surface (604) is positioned to engage front surface (207) of backrest (206), while front surface (606) is positioned to engage the back and head of a patient who is seated in chair (200). Support assembly (600) defines a pair of channels (602) that are configured to receive the prongs of frame (504). When frame (504) is inserted in channels (602), field generators (506) on the prongs of frame (504) are embedded within the body of support assembly (600); while the upper-most field generator (506) is exposed relative to the body of support assembly (600). Such a configuration may allow an operator to insert and remove frame (504) into and out of support assembly (600) with relative ease.

As best seen in FIG. 18, front surface (606) extends along a plane ($P_2$). Channels (602) are configured to orient frame (504) along another plane ($P_1$). In the present example, support assembly (600) is configured such that plane ($P_1$) is parallel with plane ($P_2$). It should be understood that planes ($P_1$, $P_2$) may also be substantially parallel with the coronal plane of a patient's head resting on support assembly (600).

In the present example, the foam material forming support assembly (600) is configured such that the material does not have a significant adverse impact on the electromagnetic field generated by field generators (506). Various suitable materials that may be used to form support assembly (600) will be apparent to those of ordinary skill in the art in view of the teachings herein.

As shown in FIG. 16, support assembly (600) of this example extends all the way down to bottom support (204) of chair (200). In some other versions, support assembly (600) only extends along the vertical height of headrest (208). In either case, straps and/or other features may be used to removably secure support assembly (600) relative to backrest (206) and/or headrest (208).

D. Fourth Exemplary Support Assembly

Figure 20:
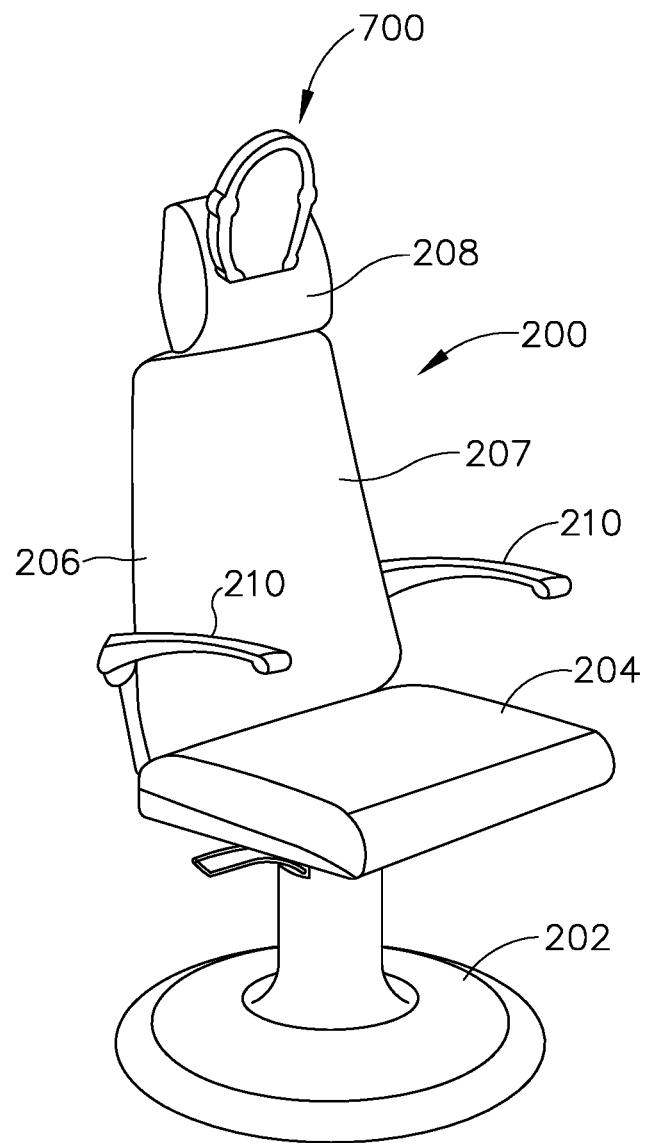
FIG. 20 depicts a perspective view of the chair of FIG. 4, with another exemplary navigation support assembly.
Figure 21:
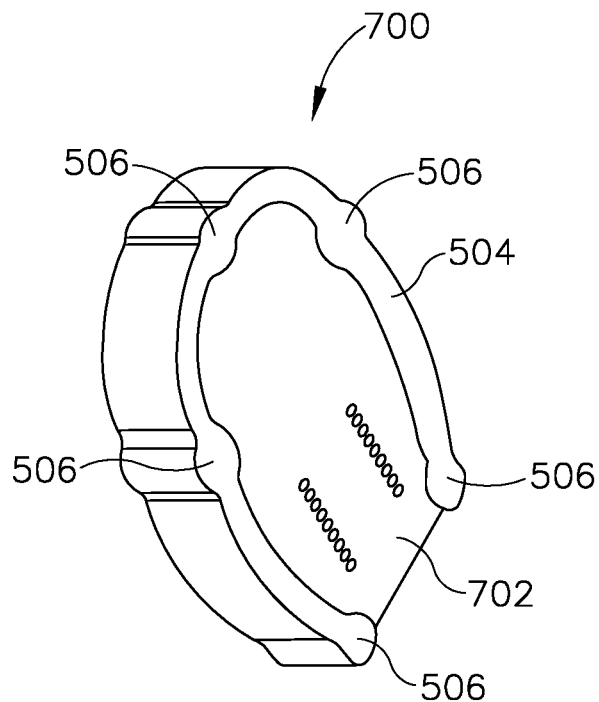
FIG. 21 depicts a perspective view of the navigation support assembly of FIG. 20.
Figure 22:
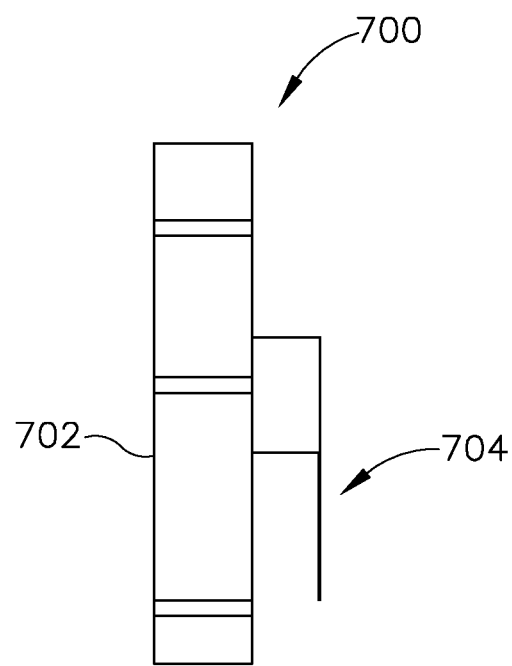
FIG. 22 depicts a side elevational view of the navigation support assembly of FIG. 20.

FIGS. 20-22 show another exemplary alternative support assembly (700) that comprises a body (702) and a coupling assembly (704) that enables body (702) to be removably secured to a headrest (208) of a conventional chair (200). Support assembly (700) is thus configured such that a patient seated in chair (200) will rest their head on support assembly (700).

In some versions, frame (504) is fully embedded within body (702). Body (702) may comprise a foam material encompassed by a flexible fabric material or other kind of material that contains the foam and frame (504). Body (702) may also include a rigid backing plate and/or other component(s) to provide additional structural integrity to support assembly (700). Body (702) the material that encompasses body (702) and frame (504) may be formed of a material that does not adversely affect the electromagnetic fields generated by field generators (506). Various suitable materials that may be used will be apparent to those of ordinary skill in the art in view of the teachings herein. In some versions, body (702) defines one or more air pockets to provide cushioning for the head of the patient. Such an air pocket or air pockets may be used in addition to or in lieu of a foam material.

Coupling assembly (704) of the present example comprises at least one strap that is operable to removably secure body (702) to chair (200). In some other versions, coupling assembly (704) comprises a clamp and/or other feature(s) to removably secure body (702) to chair (200). In addition, or in the alternative, support assembly (700) may define a pocket that is configured to insertingly receive headrest (208), such that support assembly (700) may simply be slid over headrest (208). Other suitable ways in which coupling assembly (704) may be removably secured to headrest (208) will be apparent to those of ordinary skill in the art in view of the teachings herein.

E. Fifth Exemplary Support Assembly

Figure 23:
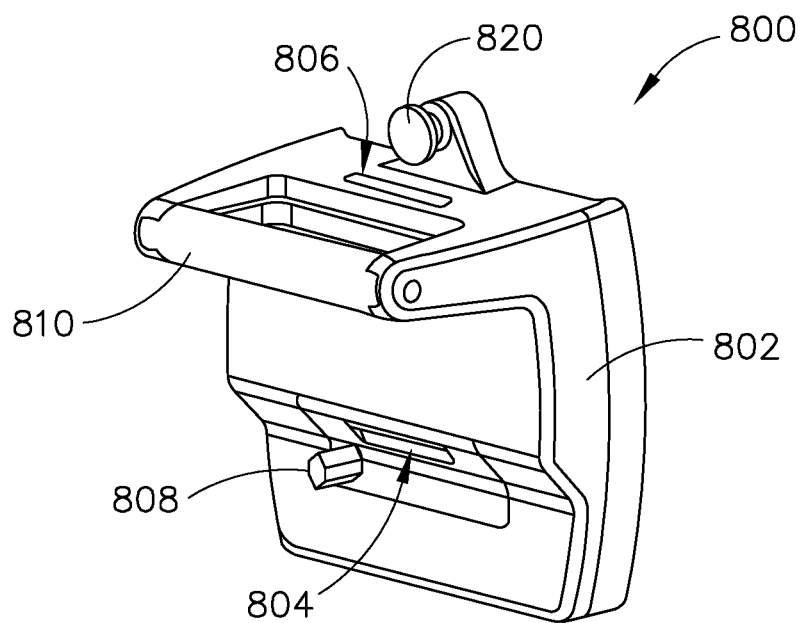
FIG. 23 depicts a perspective view of an exemplary headrest support assembly of another exemplary navigation support assembly that may be secured to the chair of FIG. 4.
Figure 24:
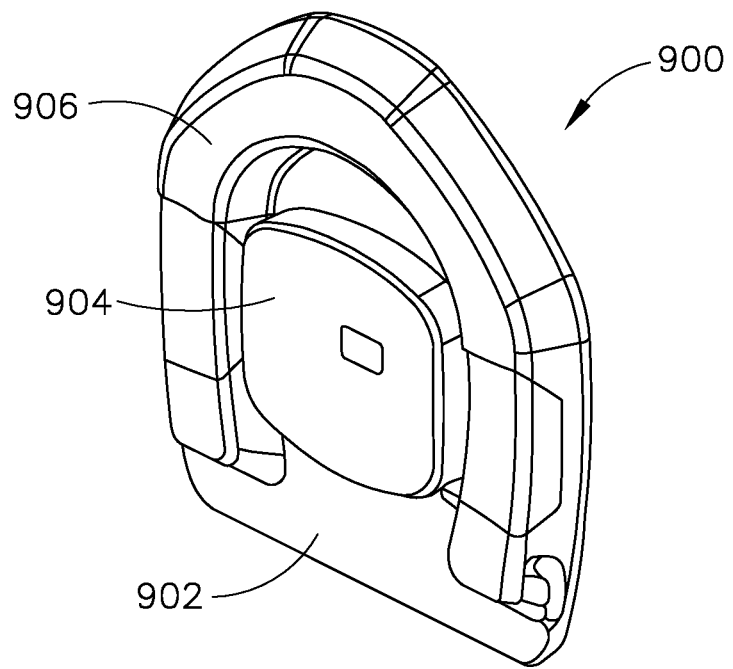
FIG. 24 depicts a perspective view of an exemplary headrest assembly that may be secured to the headrest support assembly of FIG. 23.
Figure 25:
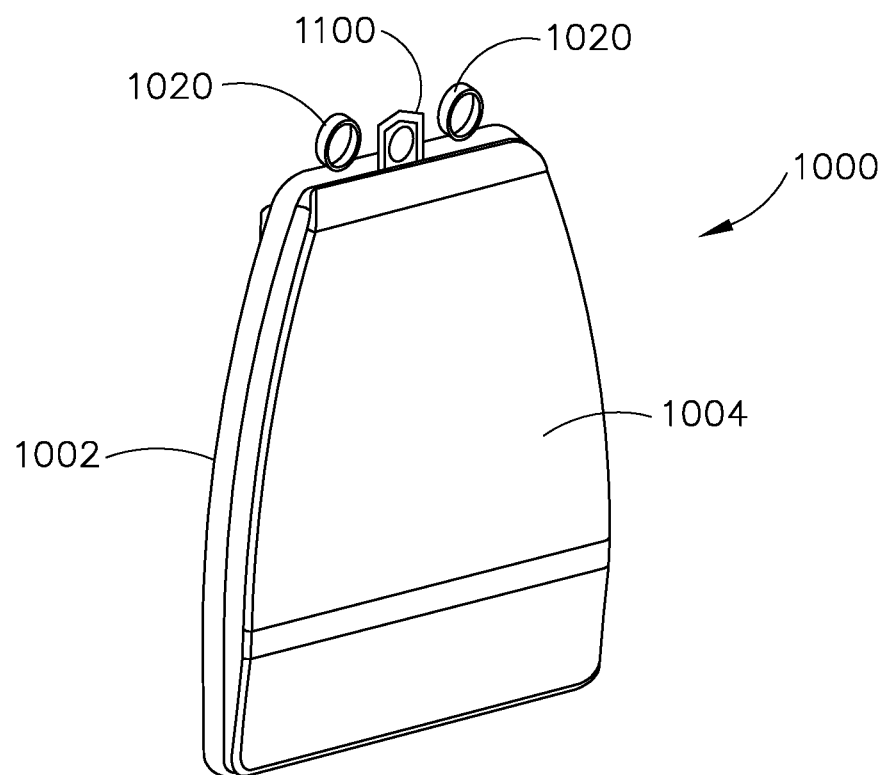
FIG. 25 depicts a perspective view of an exemplary backrest assembly that may be secured to the headrest support assembly of FIG. 23.
Figure 26:
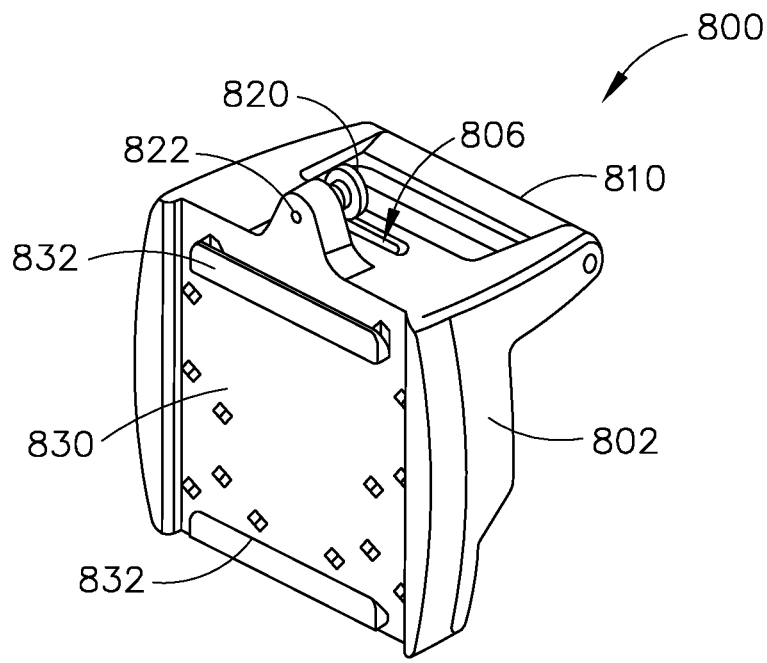
FIG. 26 depicts another perspective view of the headrest support assembly of FIG. 23.

FIGS. 23-25 show components (800, 900, 1000) of another exemplary support assembly that may be coupled with a chair like chair (200). This assembly includes a headrest support assembly (800) (FIG. 23), a headrest assembly (900) (FIG. 24), and a backrest assembly (1000) (FIG. 25). As described in greater detail below, headrest assembly (900) is configured to be secured to headrest support assembly (800); and headrest support assembly (800) is configured to be secured to backrest assembly (1000). As will also be described in greater detail below, backrest assembly (1000) is configured to be secured to backrest (206) of a conventional chair (200). In some versions, headrest assembly (900) is configured to be secured to headrest (208) of chair (200).

As shown in FIGS. 23 and 26-29B, headrest support assembly (800) of this example comprises a body (802) defining a lower opening (804) and an upper opening (806). A release button (808) projects proximally from body (802) and is configured to be pressed distally relative to body (802). A handle (810) also projects proximally from body (802) and partially contains a locking member (812), which is configured to be pulled proximally relative to body (802) and relative to handle (810). As will be described in greater detail below, headrest support assembly (800) of the present example is configured such that release button (808) must be depressed distally in order to enable locking member (812) to be pulled proximally.

Headrest support assembly (800) of the present example further includes a headrest lock knob (820) and corresponding pin (822), both of which are configured to translate relative to body (802) as will be described in greater detail below. Headrest assembly (800) further includes a distal plate (830) defining a pair of French cleat hanger features (832). As will be described below, French cleat hanger features (832) are configured to mate with complementary French cleat hanger features (912) of headrest assembly (900) to enable headrest support assembly (800) to provide structural support to headrest assembly (900).

Figure 27:
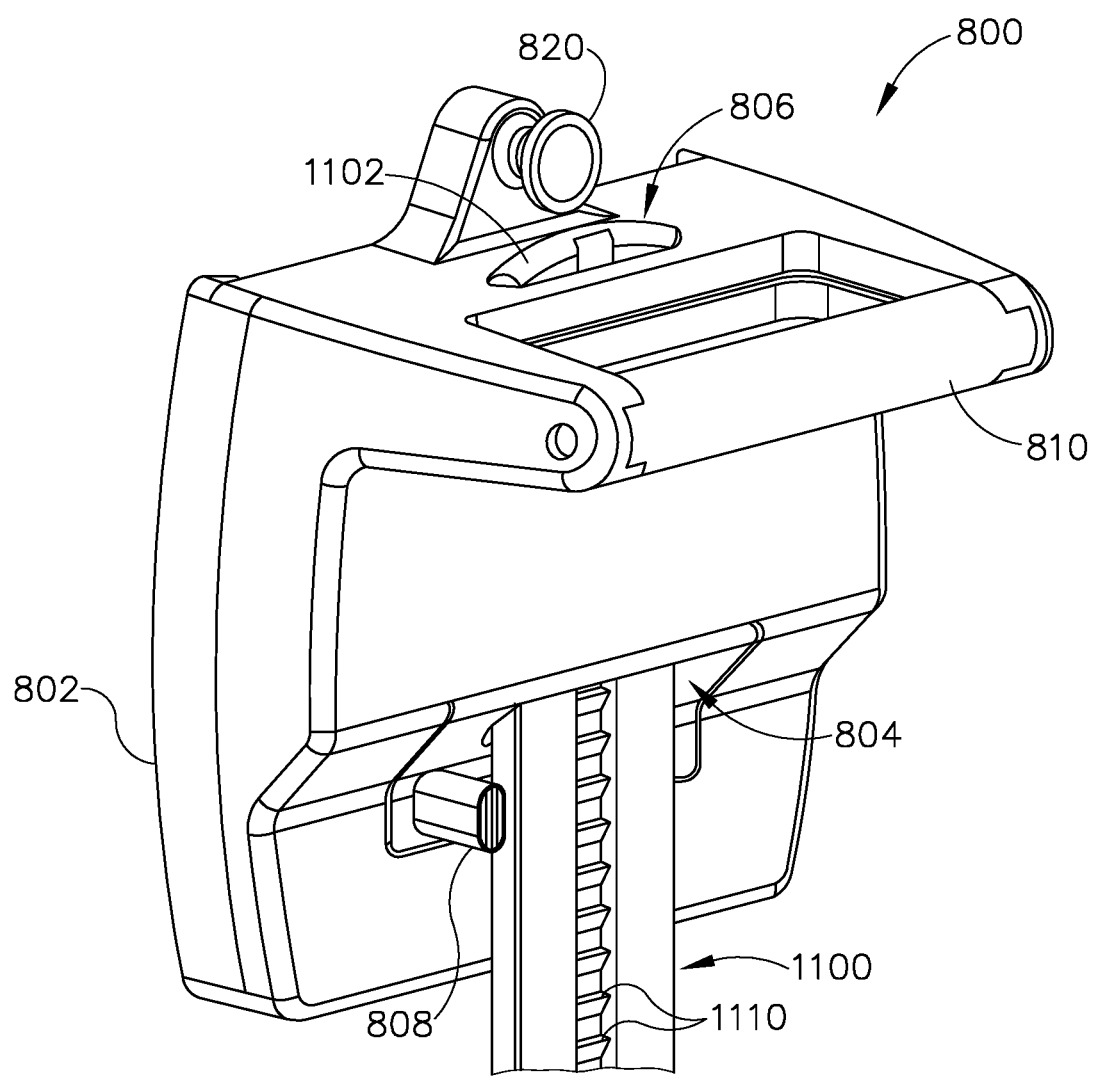
FIG. 27 depicts a perspective view of the headrest support assembly of FIG. 23 secured to a support member of the backrest assembly of FIG. 25.
Figure 28:
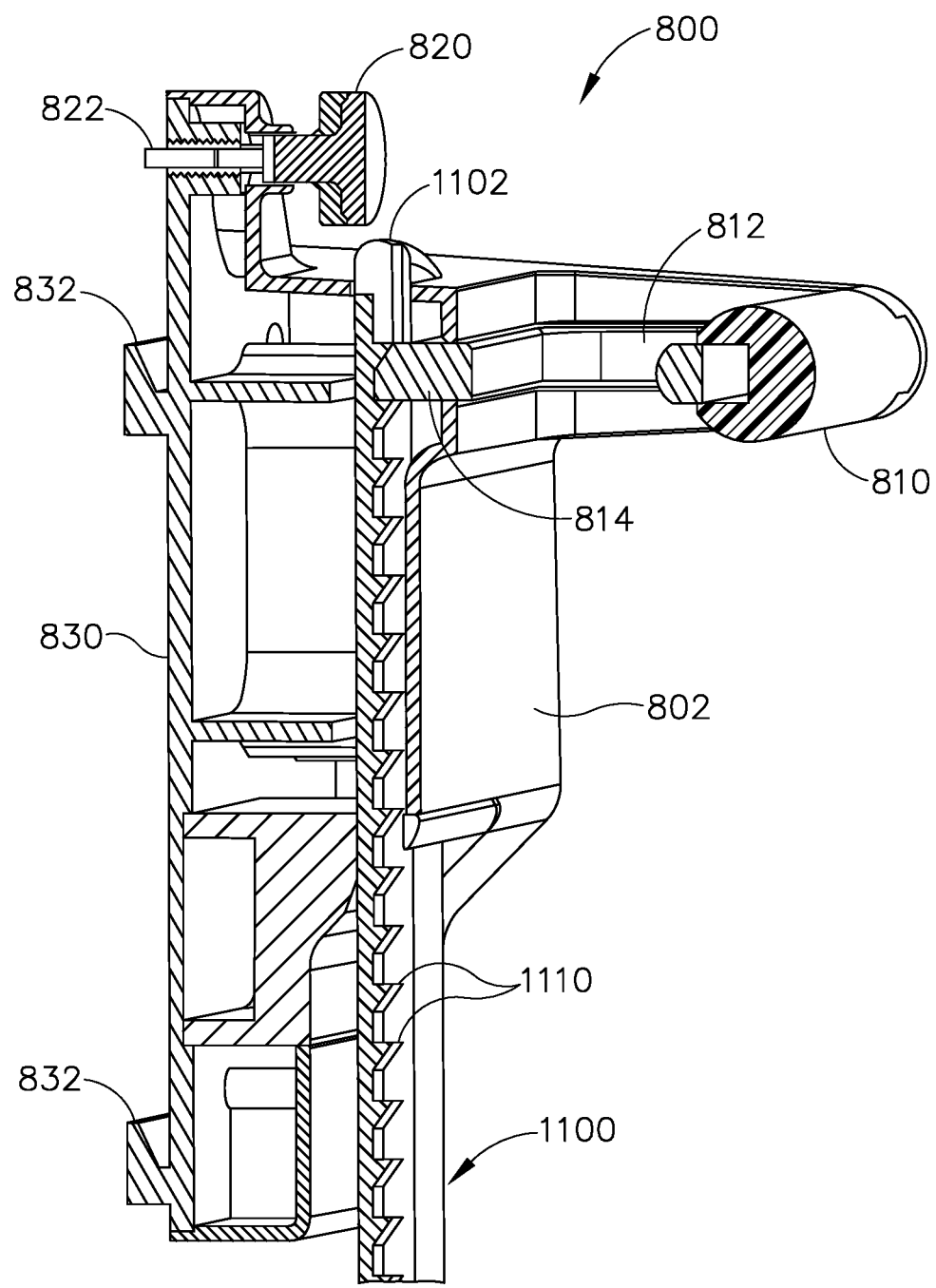
FIG. 28 depicts a perspective cross-sectional view of the headrest support assembly of FIG. 23 secured to the support member of FIG. 27.

As shown in FIGS. 27-28, a support track (1100) is inserted through openings (804, 806), providing slidable engagement between support track (1100) and body (802). Support track (1100) includes an array of proximally projecting teeth (1110). As shown in FIG. 28, locking member (812) includes a distally presented pawl feature (814). Pawl feature (814) is configured to engage teeth (1110) to thereby secure the longitudinal position of headrest support assembly (800) along the length of support track (1100). In the present example, pawl feature (814) and teeth (1110) include complementary angled surfaces that enable pawl feature (814) to ratchet along teeth (1110) as headrest support assembly (800) is slid upwardly along support track (1100); though these angled surfaces do not permit headrest support assembly (800) to be slid downwardly along support track (1100) unless locking member (812) is translated to a proximal position. As noted above, locking member (8120) is coupled with release button (808) such that release button (808) must be depressed distally in order to enable locking member (812) to be translated to a proximal position. In the present example, locking member (812) is resiliently biased toward a distal, locked position; while release button (808) is resiliently biased toward a proximal, locked position. Various suitable ways in which release button (808) may be coupled with locking member (812) will be apparent to those of ordinary skill in the art in view of the teachings herein.

As will be described in greater detail below, support track (1100) extends upwardly from backrest assembly (1000), such that support track (1100) couples headrest support assembly (800) with backrest assembly (1000). In some instances, the operator may wish to adjust the vertical height of headrest support assembly (800) relative to backrest assembly (1000) (e.g., to accommodate patients of different heights, etc.). In order to make such an adjustment, the operator may depress release button (808) distally and then pull locking member (812) proximally to disengage pawl feature (814) from teeth (1110). With release button (808) and locking member (812) so actuated, the operator may then slide headrest support assembly (800) along support track (1100) until headrest support assembly (800) reaches the desired position. The operator may then release locking member (812) to re-engage pawl feature (814) with teeth (1110) to secure the vertical position of headrest support assembly (800) along support track (1100); then release the release button (808) to secure the position of locking member (812). In instances where the operator only wishes to move headrest support assembly (800) upwardly along support track (1100), the operator may simply grasp handle (810) and thereby move headrest support assembly (800) upwardly along support track (1100), without having to pull locking member (812) proximally. In some such instances, the operator must still depress release button (808) distally. Pawl member (814) may ratchet along teeth (1110) as headrest support assembly (800) is moved upwardly.

Figure 29A:
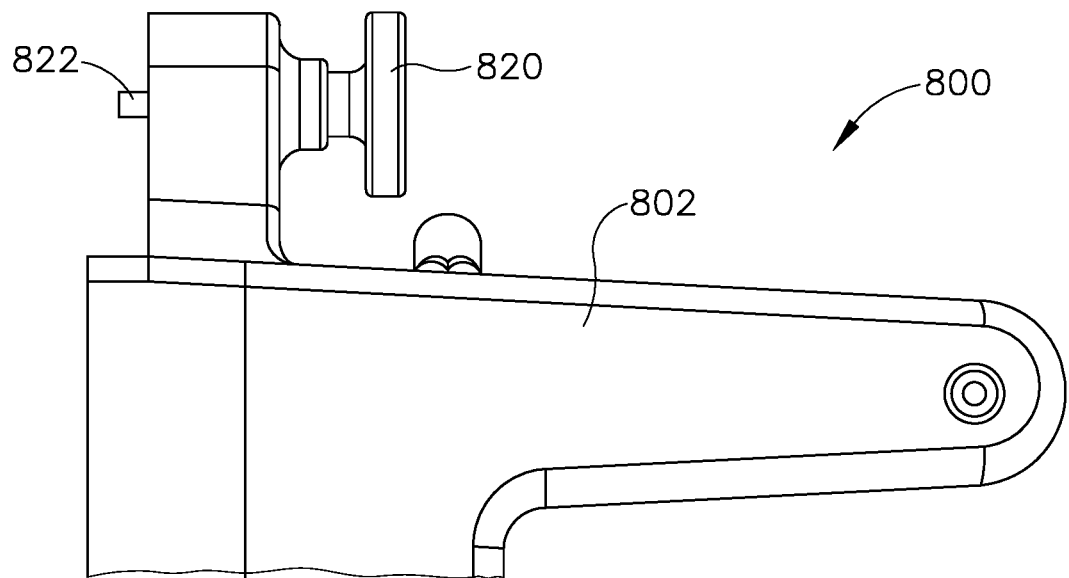
FIG. 29A depicts a side elevational view of a portion of the headrest support assembly of FIG. 23, with a headrest assembly lock in a locked position.
Figure 29B:
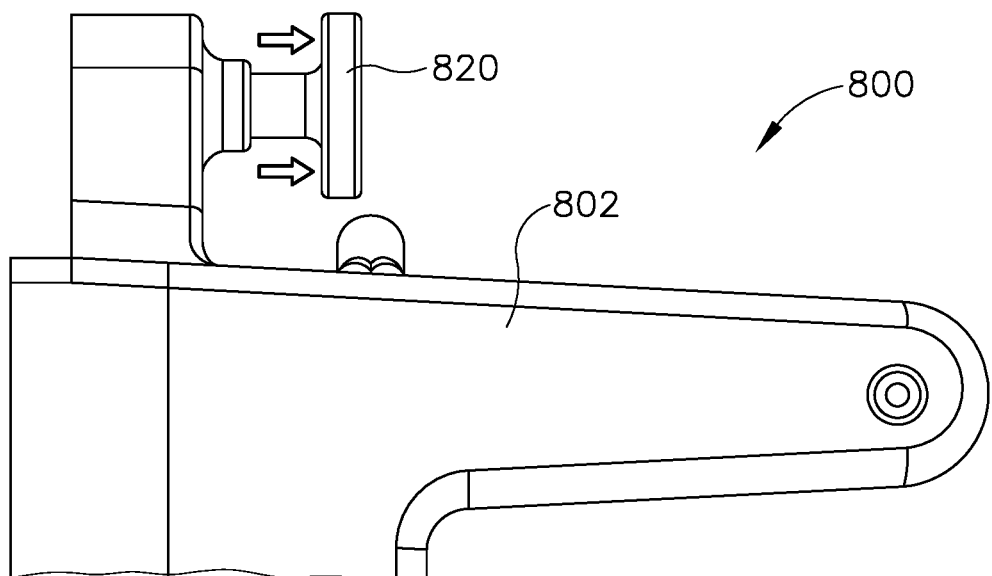
FIG. 29B depicts a side elevational view of a portion of the headrest support assembly of FIG. 23, with the headrest assembly lock in an unlocked position.

As shown in FIGS. 29A-29B, lock knob (820) and pin (822) are configured to translate relative to body (802) between a distal position (FIG. 29A) and a proximal position (FIG. 29B). In the present example, lock knob (820) and pin (822) are resiliently biased toward the distal position (e.g., by a coil spring, etc.). When pin (822) is in the distal position, pin (822) is positioned for receipt in a pin opening (914) of headrest assembly (900), which will be described in greater detail below. When pin (822) is positioned in pin opening (914), headrest assembly (900) is thereby secured to headrest support assembly (800). When pin (822) is in the proximal position, pin (822) is no longer disposed in pin opening (914), and headrest assembly (900) may be removed from headrest support assembly (800). In addition, pin (822) may be held in the proximal position when headrest assembly (900) is being initially secured to headrest support assembly (800).

In the present example, due to the positioning of lock knob (820), lock knob (820) may be retracted to the proximal position (FIG. 29B) only when headrest support assembly (800) is at a maximum height along support track (1100), where upper end (1102) of support track (1100) is effectively lower than the bottom edge of lock knob (820). When headrest support assembly (800) is at a position below the maximum height along support track (1100), support track (1100) will prevent lock knob (820) from translating to the proximal position by physically obstructing lock knob (820). In some other versions, features providing locking engagement between headrest assembly (900) and headrest support assembly (800) are not affected by the vertical position of headrest support assembly (800) along support track (1100).

Figure 30:
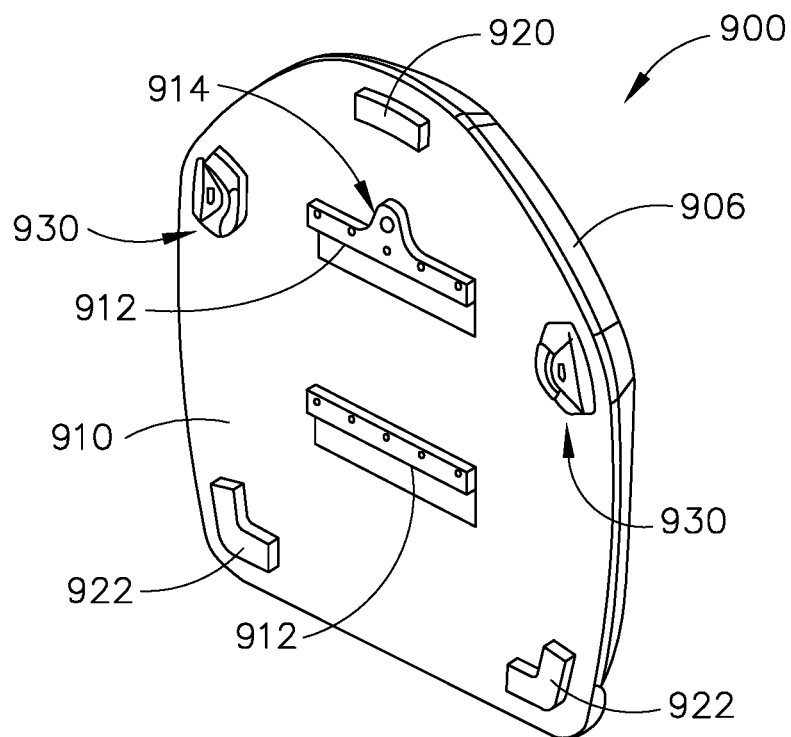
FIG. 30 depicts another perspective view of the headrest assembly of FIG. 24.
Figure 31:
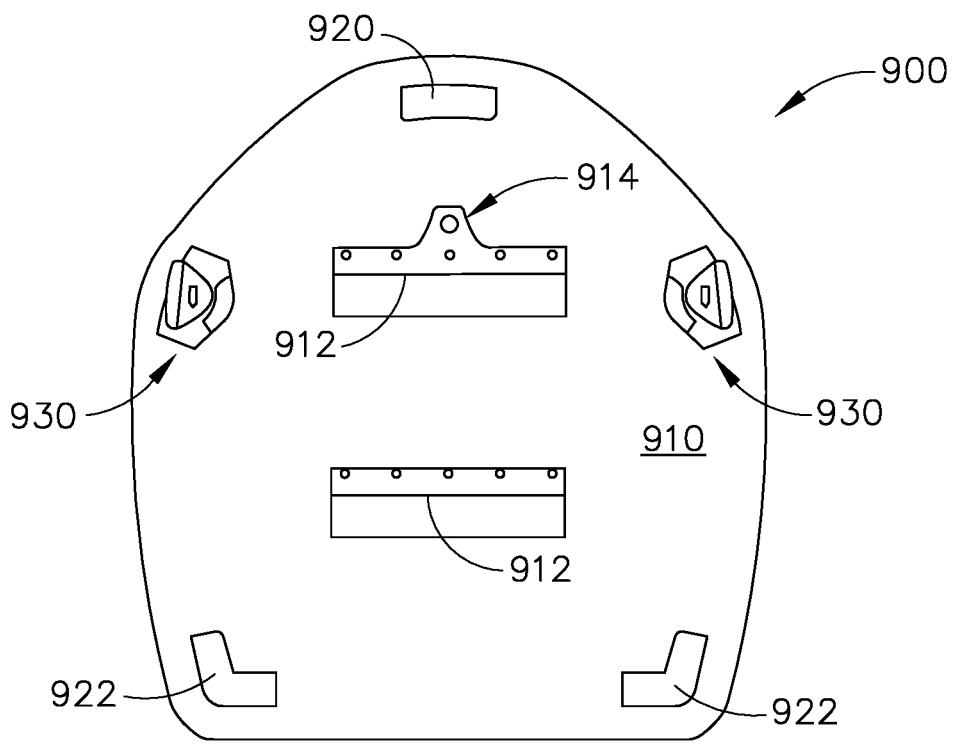
FIG. 31 depicts a rear elevational view of the headrest assembly of FIG. 24.

As shown in FIGS. 24 and 30-33, headrest assembly (900) of this example comprises a shoulder cushion (902), a head cushion (904), a rigid body (906), a rigid rear plate (910), and an intermediate plate (940). Cushions (902, 904) are configured to provide cushioned support to the shoulders and head of a patient. Intermediate plate (940) is interposed between body (906) and rear plate (910). Various components are securely mounted to intermediate plate (940), including French cleat hanger features (912), bumpers (920, 922), and strap support assemblies (930). Rear plate (910) includes openings that allow these components (912, 920, 922, 930) to protrude proximally relative to rear plate (910). As best seen in FIGS. 30-31, pin opening (914) is disposed above the upper French cleat hanger feature (912). In order to secure headrest assembly (900) to headrest support assembly (800) in the present example, an operator may hold lock knob (820) in a proximal position (FIG. 29B) and engage French cleat hanger features (912) with French cleat hanger features (832); then release lock knob (820) to enable pin (822) to enter pin opening (914). Cooperation between French cleat hanger features (832, 912), and between pin (822) and pin opening (914), will secure headrest assembly (900) to headrest support assembly (800).

Figure 32:
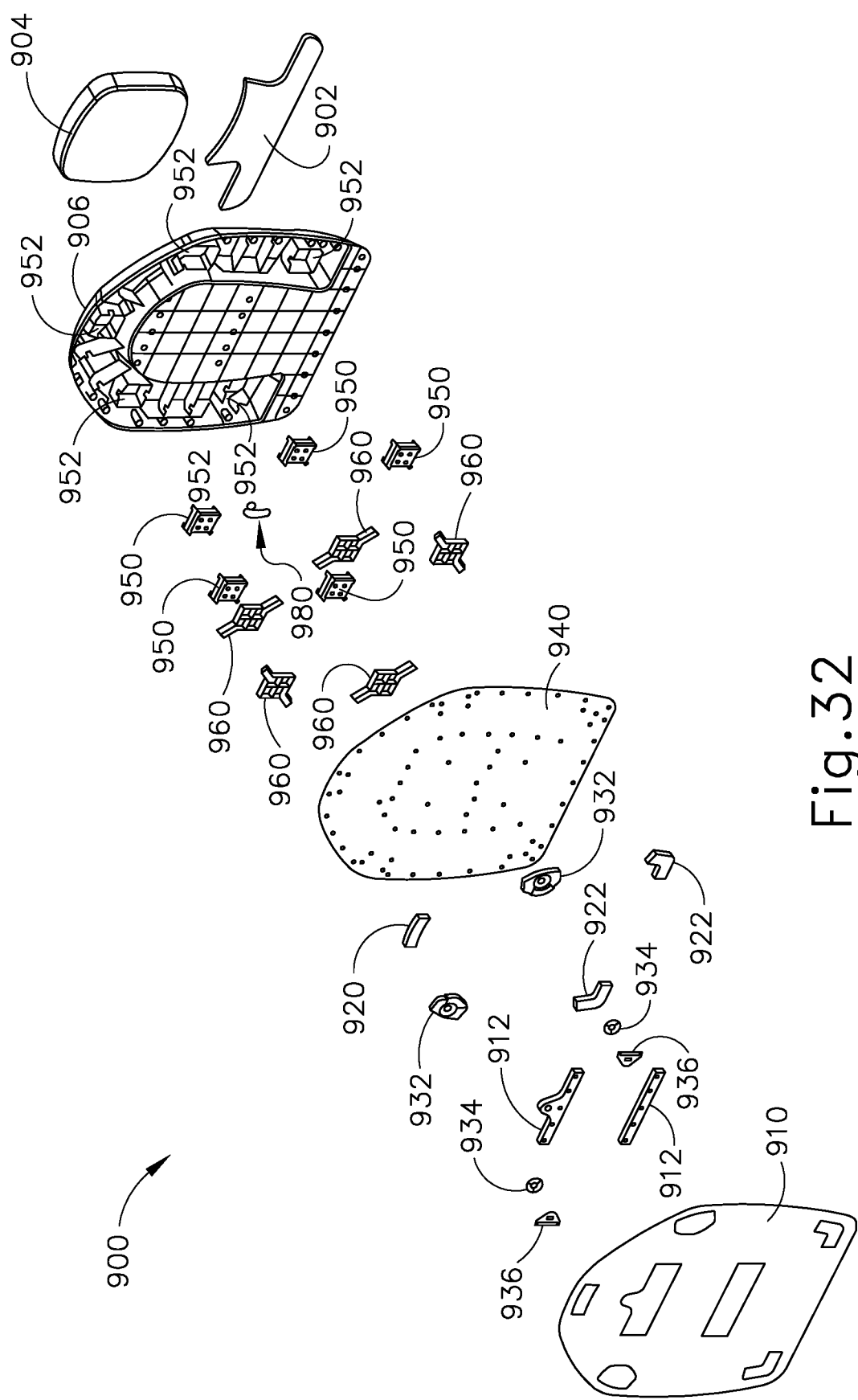
FIG. 32 depicts an exploded perspective view of the headrest assembly of FIG. 24.
Figure 33:
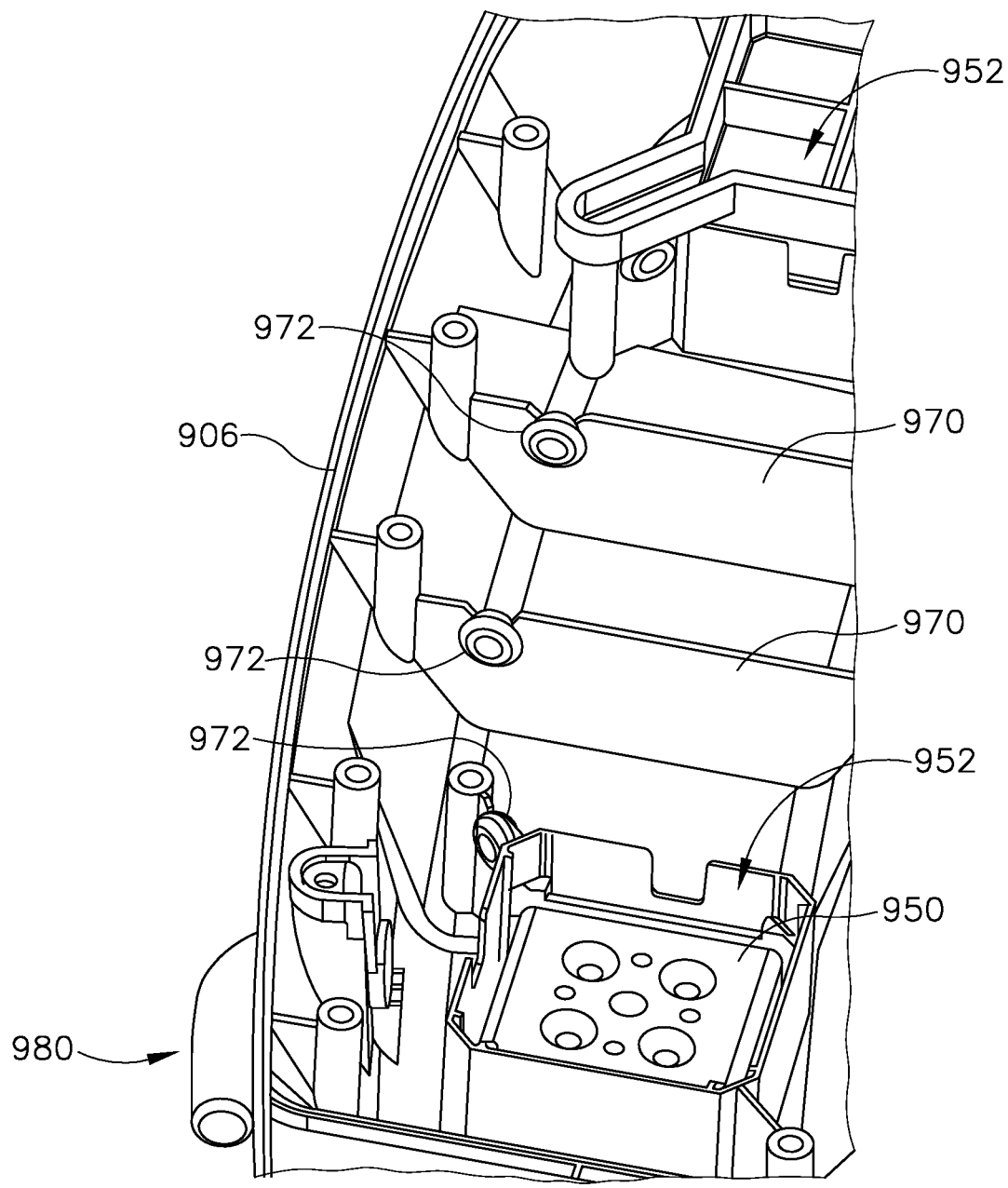
FIG. 33 depicts a perspective view of a portion of the headrest assembly of FIG. 24.

As shown in FIG. 32, body (906) of the present example defines a plurality of bobbin recesses (952). In the present example, body (906) defines five bobbin recesses (952) along a U-shaped arc that corresponds with the configuration of frame (504) and field generators (506). A plurality of square shaped bobbins (950) are disposed in bobbin recesses (952), such that each recess (952) contains a respective bobbin (950). A corresponding set of retainers (960) are secured to body (906) to thereby retain bobbins (950) in recesses (952). Each bobbin (950) has one or more wires (not shown) wrapped around bobbin (950) to form a coil configuration. These wires are fed through grommets (972), which are disposed in structural webs (970) of body (906). The wires ultimately exit body (906) via a strain relief assembly (980). The wires may be coupled with IGS navigation system (100). Each bobbin (950) wrapped in wire may this serve as a field generator, just like field generators (122, 506) described above.

Each strap support assembly (930) comprises a bumper (932), an anchor base (934), and a swivel plate (936). Bumper (932) and anchor base (934) are fixedly secured to intermediate plate (940). Swivel plate (936) is pivotably coupled to anchor base (934) such that swivel plate (936) is operable to rotate relative to anchor base (934). As will be described in greater detail below, swivel plate (936) is configured to couple with a strap assembly (1200), which may be used to further secure headrest assembly (900) to a headrest (208) of a chair (200). In some variations, headrest assembly (900) is secured to a headrest (208) of a chair (200), without also being coupled with headrest support assembly (800). In other words, headrest support assembly (800) (and even backrest assembly (1000)) may be omitted when headrest assembly (900) is secured directly to a headrest (208) of a chair (200) via strap assembly (1200) and strap support assemblies (930). In some other versions, strap support assemblies (930) are omitted from headrest assembly (900).

Figure 34:
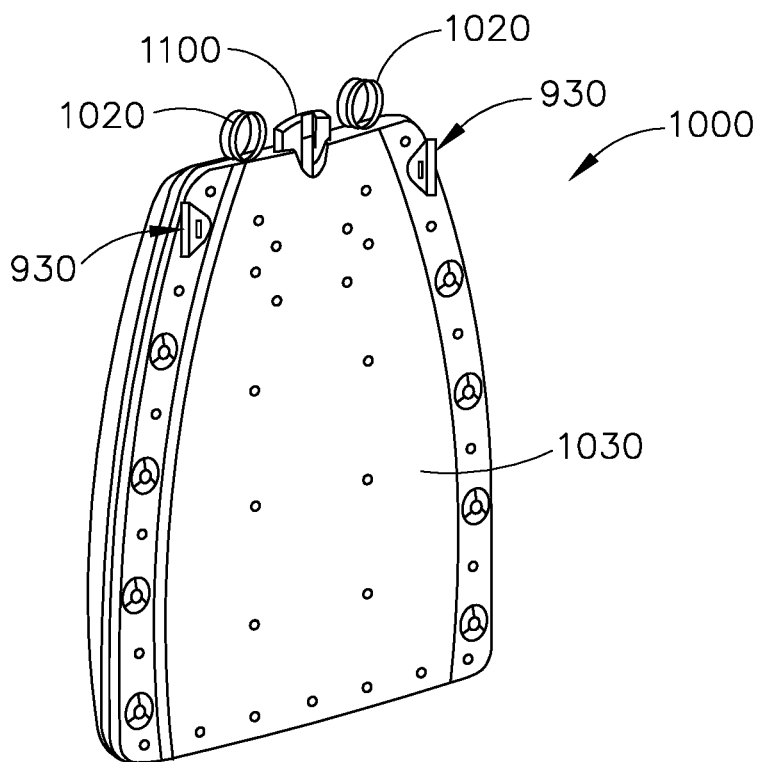
FIG. 34 depicts another perspective view of the backrest assembly of FIG. 25.
Figure 35:
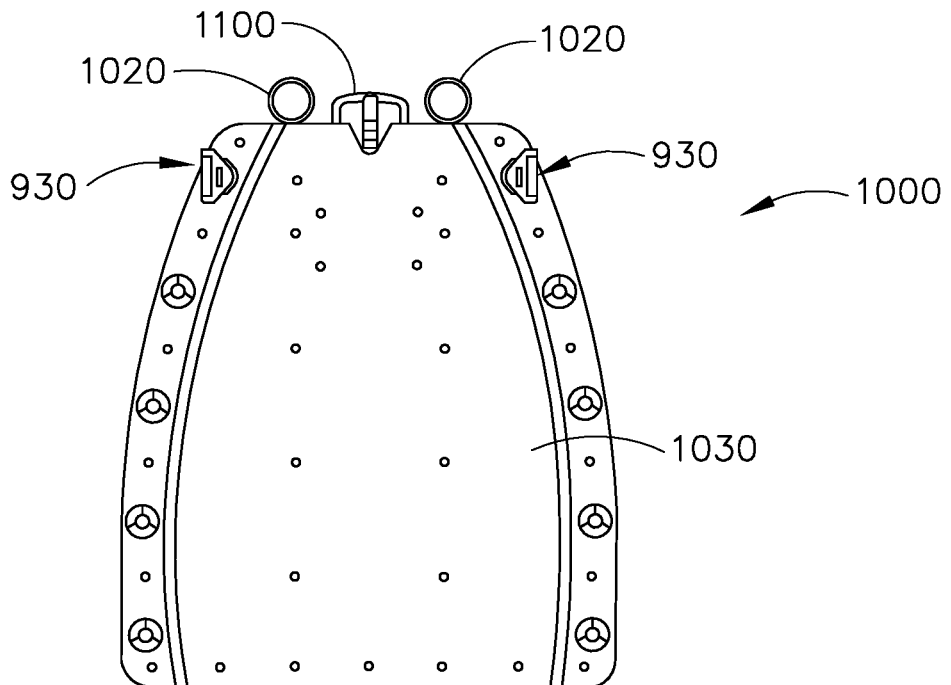
FIG. 35 depicts a rear elevational view of the backrest assembly of FIG. 25.

As shown in FIGS. 25 and 34-40, backrest assembly (1000) of this example comprises a shell assembly (1002), a front cushion (1004), and a pair of actuators (1020). Front cushion (1004) is positioned and configured to engage a back of a patient. Shell assembly (1002) comprises a front shell (1006) and a rear shell (1030). A plurality of strap support assemblies (930) are secured to the proximal side of rear shell (1030). FIGS. 34-35 show swivel plates (936) on only the uppermost pair of strap support assemblies (930) on rear shell (1030); only showing anchor bases (934) on the rest of strap support assemblies (930) on rear shell (1030). It should be understood that these additional anchor bases (934) may also have swivel plates (936) coupled thereto.

Figure 36:
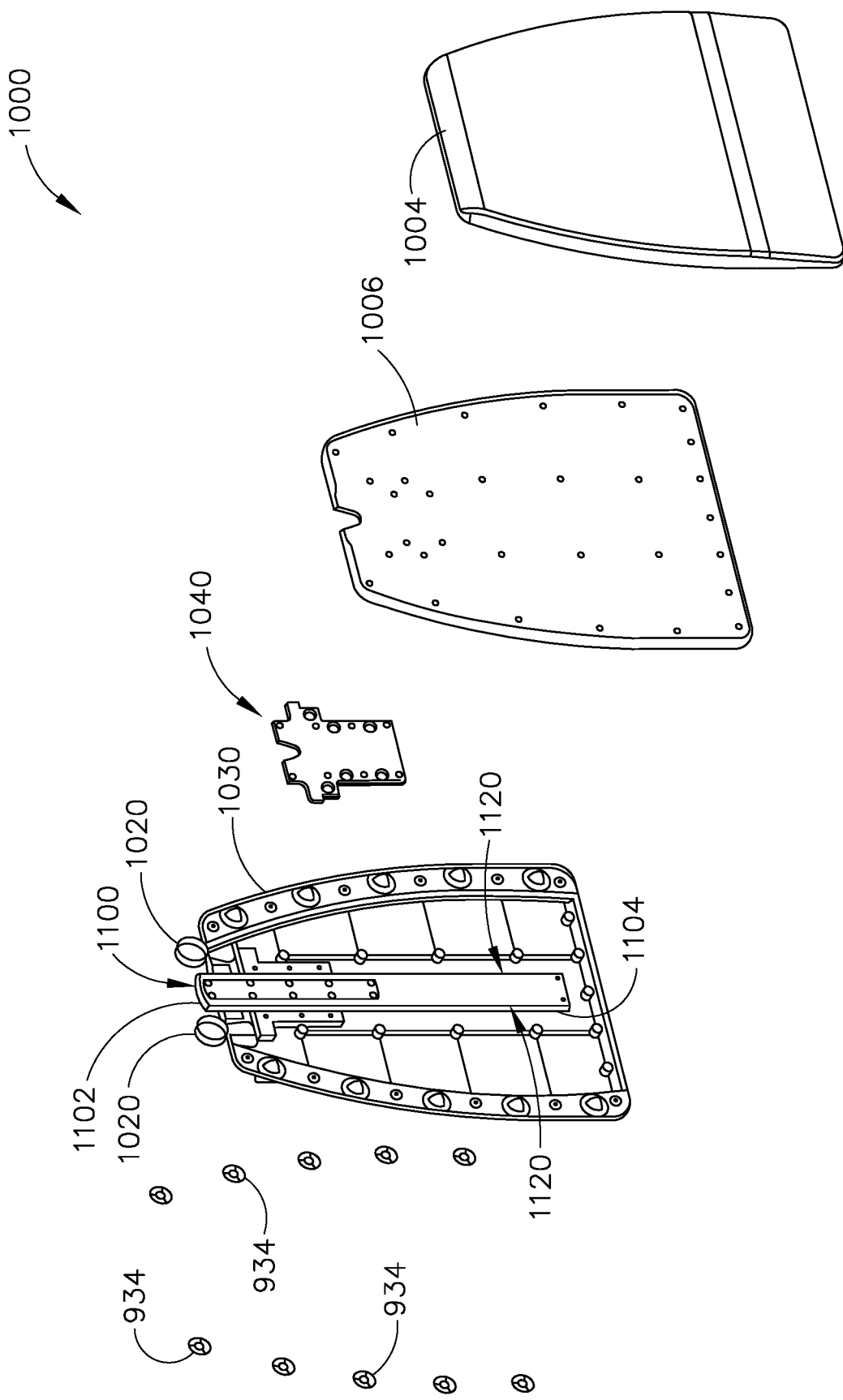
FIG. 36 depicts an exploded perspective view of the backrest assembly of FIG. 25.

As best seen in FIG. 36, support track (1100) is slidably disposed in a corresponding recess formed in rear shell (1030). FIG. 36 shows support track (1100) in a lower position, where upper end (1102) of support track (1100) is near the top of rear shell (1030) and lower end (1104) of support track (1100) is near the bottom of rear shell (1030). A retaining plate (1040) is secured to rear shell (1030) near the upper end of rear shell (1030), securing support track (1100) to rear shell (1030) while still permitting support track (1100) to slide relative to rear shell (1030). As also seen in FIG. 36, support track (1100) defines a pair of lateral notches (1120) near lower end (1104) of support track (1100).

Figure 37A:
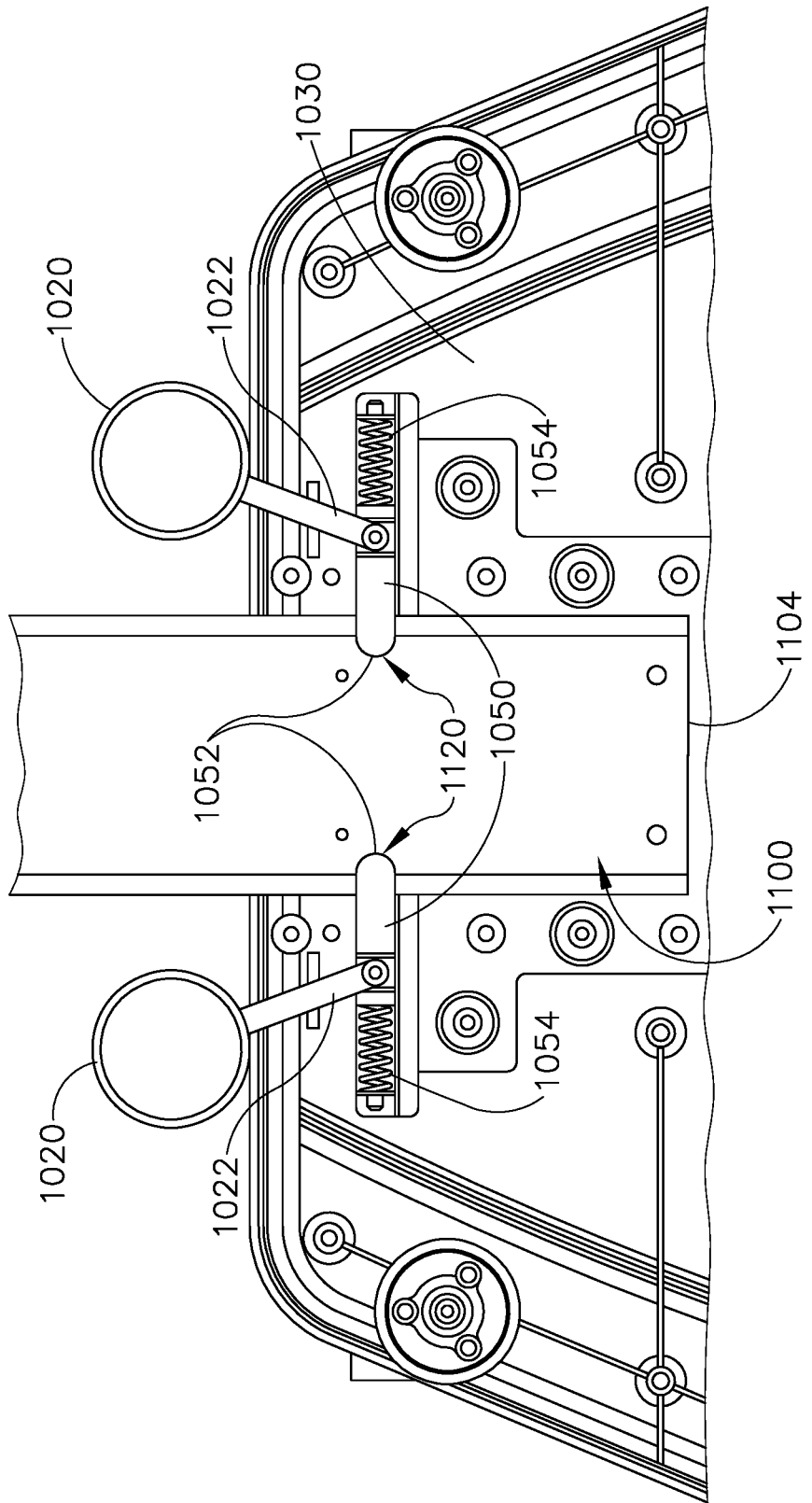
FIG. 37A depicts a front elevational view of a portion the backrest assembly of FIG. 25, showing locking features engaged with the support member of FIG. 27.
Figure 37B:
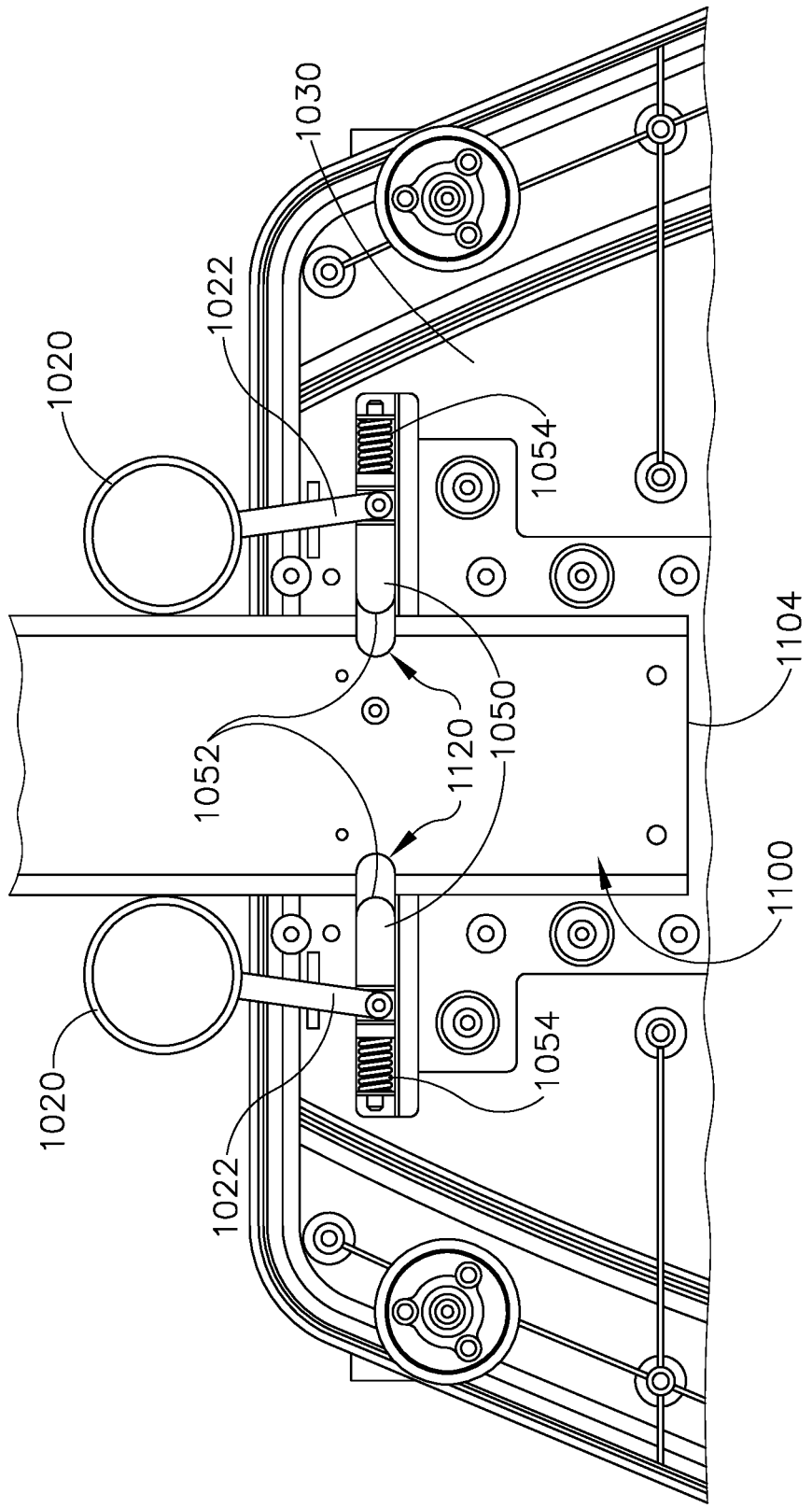
FIG. 37B depicts a front elevational view of the portion of the backrest assembly of FIG. 37A, showing the locking features disengaged from the support member of FIG. 27.

As best seen in FIGS. 37A-37B, actuators (1020) are in the form of rings that are sized to accommodate an operator's fingers. Each actuator (1020) is coupled with a corresponding arm (1022), which is in turn pivotably coupled with a lock pin (1050). Each lock pin (1050) has a free end (1052) that is configured to fit in a corresponding lateral notch (1120) near lower end (1104) of support track (1100). FIG. 37A shows support track (1100) in an upper position, where lower end (1104) of support track (1100) is near the top of rear shell (1030) and lock pins (1050) secure support track (1100) in this upper position. In some instances, after reaching the state shown in FIG. 37A, the operator may wish to retract support track (1100) back into backrest assembly (1000) (e.g., to transport, store, or dispose of backrest assembly, etc.). In order to retract support track (1100) back into backrest assembly (1000), the operator may urge actuators (1020) inwardly toward each other (simultaneously) to disengage lock pins (1050) from lateral notches (1020), as shown in FIG. 37B. With lock pins (1050) disengaged from lateral notches (1020), the operator may then urge support track (1100) downwardly into backrest assembly (1000). In some versions, the upper portion of support track (1100) also includes lateral notches, such that the operator may position lock pins (1050) in these upper lateral notches to secure support track (1100) in the retracted position relative to backrest assembly (1000).

In the present example, a pair of coil springs (1054) resiliently urge lock pins (1050) inwardly toward support track (1100). Coil springs (1054) may thus resiliently urge lock pins (1050) into engagement with lateral notches (1020). In addition, when the operator actuates actuators (1020) to retract support track (1100) into backrest assembly (1000), coil springs (1054) may continue to urge free ends (1052) into engagement with the lateral edges of support track (1100) to provide friction to reduce the risk of support track (1100) falling freely into backrest assembly (1000).

Figure 38:
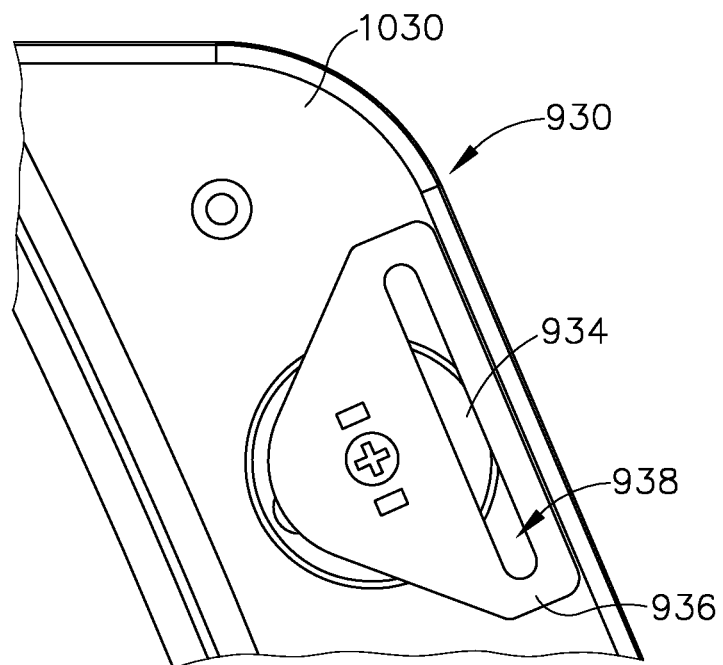
FIG. 38 depicts a rear elevational view of a strap support assembly of the backrest assembly of FIG. 25 in a first angular position.
Figure 39:
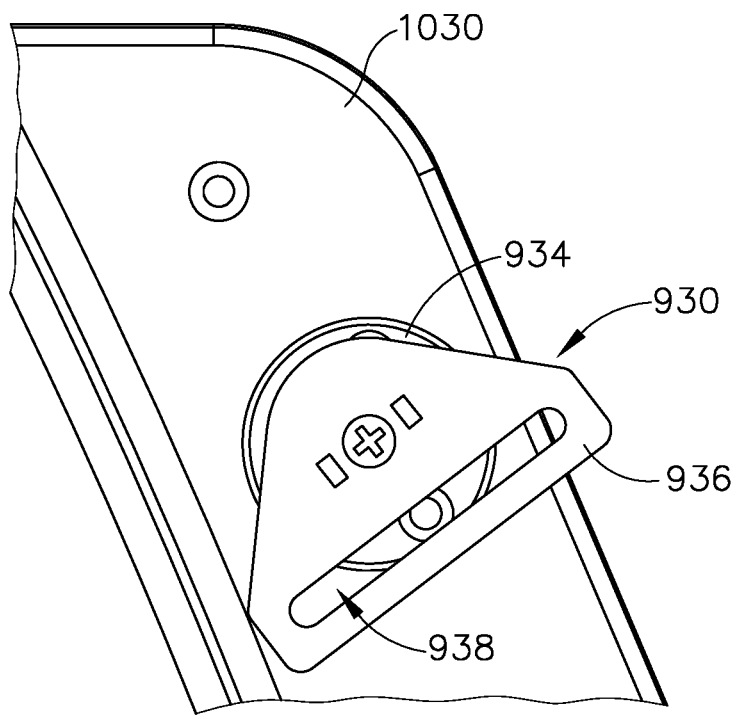
FIG. 39 depicts a rear elevational view of the strap support assembly of FIG. 38 in a second angular position.
Figure 40:
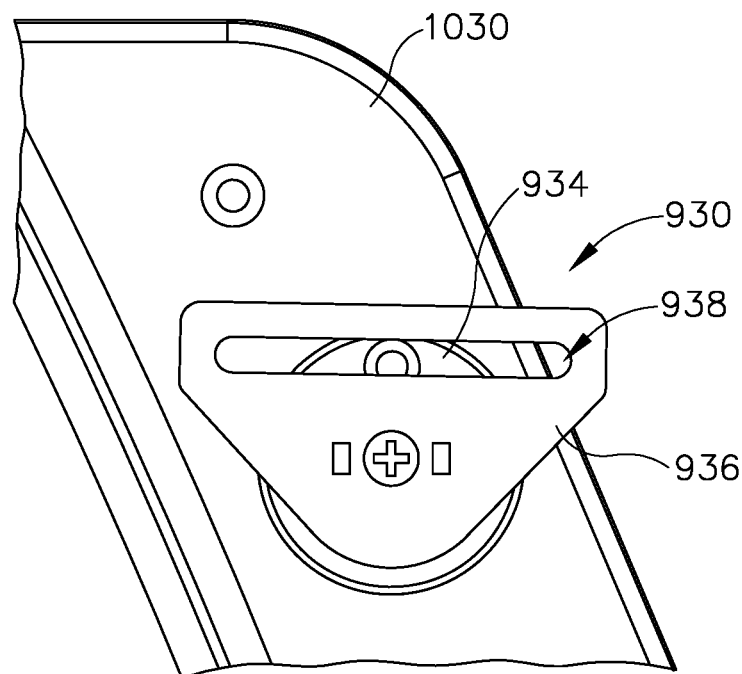
FIG. 40 depicts a rear elevational view of the strap support assembly of FIG. 38 in a third angular position.
Figure 41:
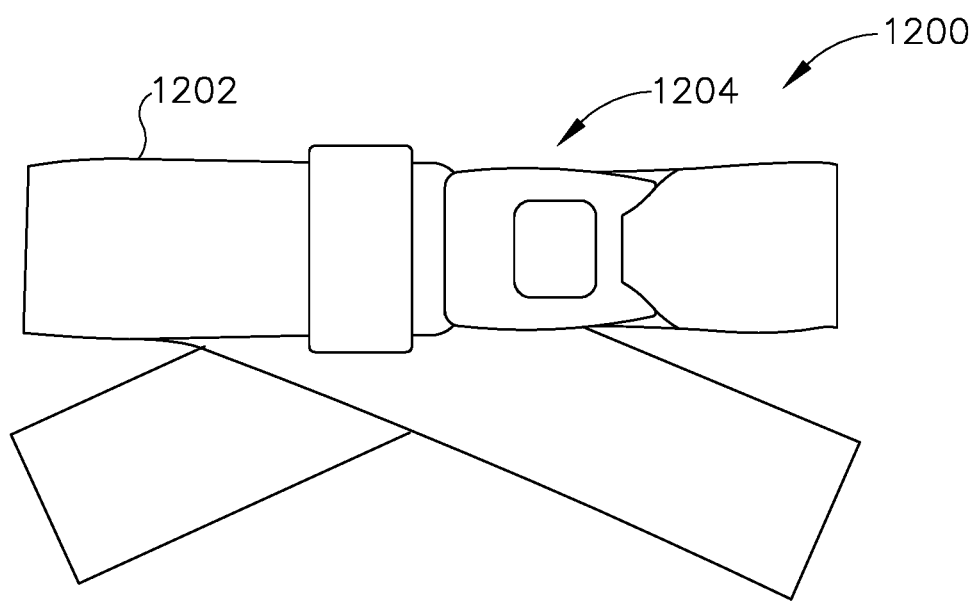
FIG. 41 depicts a top plan view of an exemplary strap assembly that may be used to secure the backrest assembly of FIG. 25 to the chair of FIG. 4 via the strap support assembly of FIG. 38.

FIGS. 38-40 show a strap support assembly (930) of rear shell (1030) at various exemplary positions. As shown, swivel plate (936) includes a slot (938) that is sized and configured to receive a webbing (1202) of a strap assembly (1200). FIG. 41 shows an exemplary form that strap assembly (1200) may take. In this example, strap assembly (1200) comprises a webbing (1202) secured to a buckle (1204). Buckle (1204) is configured to releasably secure one end of webbing (1202) relative to another end of webbing (1202). Strap assembly (1200) may also include an adjustment feature that enables the operator to adjust the effective length of strap assembly (1200). Strap assembly (1200) may comprise any suitable kind of convention strap assembly as will be apparent to those of ordinary skill in the art in view of the teachings herein. As noted above, swivel plate (936) is configured to pivot relative to anchor base (934). FIG. 38 shows one exemplary angular orientation of swivel plate (936) that may be suitable for securing backrest assembly (1000) to a backrest (206) of one kind of chair (200) using strap assembly (1200). FIG. 39 shows another exemplary angular orientation of swivel plate (936) that may be suitable for securing backrest assembly (1000) to a backrest (206) of another kind of chair (200) using strap assembly (1200). FIG. 40 shows another exemplary angular orientation of swivel plate (936) that may be suitable for securing or removing a strap assembly (1200) to or from swivel plate (936). Other suitable configurations will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body, wherein the body is configured to be positioned between a patient's back and a backrest of a chair; (b) an upright member extending upwardly from the body; (c) a frame mounted to the upright member, wherein the frame has a curved configuration configured to partially surround a patient's head; and (d) a plurality of field generating elements supported by the frame, wherein the field generating elements are configured to generate an electromagnetic field around a patient's head partially surrounded by the frame.

Example 2

The apparatus of Example 1, wherein the body has a wedge shape.

Example 3

The apparatus of Example 2, wherein the wedge shape has an upper portion and a lower portion, wherein the upper portion has a thickness that is greater than a thickness of the lower portion.

Example 4

The apparatus of Example 3, wherein the upright member extends upwardly from the upper portion.

Example 5

The apparatus of any one or more of Examples 1 through 4, wherein the upright member defines a longitudinal axis, wherein the frame is movable along the longitudinal axis of the upright member.

Example 6

The apparatus of any one or more of Examples 1 through 5, wherein the upright member defines a longitudinal axis, wherein the frame is movable along a dimension that is transverse to the longitudinal axis of the upright member.

Example 7

The apparatus of any one or more of Examples 1 through 6, further comprising a headrest secured to the upright member, wherein the headrest is configured to support a patient's head partially surrounded by the frame.

Example 8

The apparatus of any one or more of Examples 1 through 7, further comprising a plurality of tabs extending laterally relative to the body.

Example 9

The apparatus of Example 8, wherein the tabs include a plurality of slots configured to receive straps.

Example 10

The apparatus of any one or more of Examples 1 through 9, wherein the body, the upright member, and the frame consist of non-metallic materials.

Example 11

The apparatus of any one or more of Examples 1 through 10, further comprising a chair, wherein the chair comprises a bottom support and a backrest, wherein the body is positioned above the bottom support, wherein the body is engaged with the backrest.

Example 12

The apparatus of Example 11, further comprising at least one strap securing the body to the backrest.

Example 13

The apparatus of any one or more of Examples 11 through 12, wherein the frame is movable fore and aft relative to the upright member.

Example 14

The apparatus of Example 13, wherein the frame is movable fore and aft relative to the upright member along a range of motion including an aft-most position where a rear surface of the frame is approximately 15 cm from a front surface of the front surface of the backrest.

Example 15

The apparatus of any one or more of Examples 13 through 14, wherein the frame is movable fore and aft relative to the upright member along a range of motion including a foremost position where a rear surface of the frame is approximately 25 cm from a front surface of the front surface of the backrest.

Example 16

The apparatus of any one or more of Examples 1 through 15, further comprising an image guided surgery navigation system, wherein the field generating elements are coupled with the image guided surgery navigation system.

Example 17

A method comprising: (a) positioning a body of a support assembly on a backrest of a chair, above a bottom support of the chair, wherein the support assembly further includes: (i) an upright member extending upwardly from the body, a frame mounted to the upright member, wherein the frame has a curved configuration configured to partially surround a patient's head, and (ii) a plurality of field generating elements supported by the frame, wherein the field generating elements are configured to generate an electromagnetic field around a patient's head partially surrounded by the frame; (b) securing the body of the support assembly to the backrest of the chair.

Example 18

The method of Example 17, wherein the act of securing comprises securing straps to the backrest of the chair to thereby secure the body of the support assembly to the backrest of the chair.

Example 19

The method of any one or more of Examples 17 through 18, further comprising: (a) positioning a patient in the chair such that the patient's back engages the body and such that the frame partially surrounds the patient's head; and (b) activating the field generating elements to generate an electromagnetic field around the patient's head.

Example 20

The method of Example 19, further comprising: (a) viewing a navigation screen displaying positioning of a medical instrument in the patient's head, wherein the positioning display is based on data generated using the electromagnetic field; and (b) performing an operation with the medical instrument in the patient's head.

V. Miscellaneous

In some versions, at least a portion of the length of guidewire (200, 300) (e.g., approximately 7 inches) is coated in one or more materials. By way of example only, at least a portion of the length of guidewire (200, 300) may be coated in silicone. Other suitable materials that may be used as a coating for guidewire (200, 300) will be apparent to those of ordinary skill in the art in view of the teachings herein.

In some versions, the distal portion (204, 304) of guidewire (200, 300) may include a preformed bend. By way of example only, such a preformed bend may be provided in accordance with at least some of the teachings of U.S. Provisional Pat. App. No. 62/453,220, entitled "Navigation Guidewire with Interlocked Coils," filed Feb. 1, 2017, the disclosure of which is incorporated by reference herein; and/or in accordance with teachings of various other patent references cited herein.

In some versions, each version of support assembly (240, 300, 500, 600, 700, 800, 900, 1000) is formed entirely of non-metallic materials. In addition, the materials used to form support assembly (240, 300, 500, 600, 700, 800, 900, 1000) may be configured to allow easily cleaning of support assembly (240, 300, 500, 600, 700, 800, 900, 1000) with disinfectants, such that the disinfectants do not damage the materials forming support assembly (240, 300, 500, 600, 700, 800, 900, 1000). The materials used to form any portion(s) of support assembly (240, 300, 500, 600, 700, 800, 900, 1000) that may come in prolonged contact with the patient's skin may also be biocompatible and comply with cytoxicity, sensitization, and irritation tests. Various suitable materials that may be used to form support assembly (240, 300, 500, 600, 700, 800, 900, 1000) meeting at least some of the above criteria will be apparent to those of ordinary skill in the art in view of the teachings herein.

By way of further example only, the entire weight of support assembly (240, 300, 500), without frame (504) and field generators (506), may be less than approximately 50 kg. Support assembly (240, 300, 500) may also be configured to provide sufficient mechanical support to enable the combination of chair (200, 400) and support assembly (240, 300, 500) to support a patient weighing up to approximately 150 kg.

While chairs (200, 400) are provided in the examples described herein, the teachings herein may be readily used in combination with various other kinds of chairs, including but not limited to various other kinds of chairs that are designed for use in ENT procedures. Support assembly (240, 300, 500) may thus accommodate various kinds of backrest widths and other structural variations among chairs.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a supplemental backrest body, wherein the body generally defines an upright plane and is adapted to be positioned between a patient's back and a backrest of a chair, wherein the supplemental backrest body comprises a mechanism adapted for removably attaching the supplemental backrest body to the chair;
   (b) an upright member extending upwardly from the body and defining an upward sliding direction generally parallel to the upright plane;
   (c) a frame mounted to the upright member and configured for sliding adjustment in the upward sliding direction, wherein the frame has a curved configuration adapted to partially surround a patient's head; and
   (d) a plurality of field generating elements supported by the frame, wherein the field generating elements are configured to generate an electromagnetic field, the field adapted to be present in a space around a patient's head when at least partially surrounded by the frame.

2. The apparatus of claim 1, wherein the body has a wedge shape.

3. The apparatus of claim 2, wherein the wedge shape has an upper portion and a lower portion, wherein the upper portion has a thickness that is greater than a thickness of the lower portion.

4. The apparatus of claim 3, wherein the upright member extends upwardly from the upper portion.

5. The apparatus of claim 1, wherein the upright member defines a longitudinal axis, wherein the frame is movable along the longitudinal axis of the upright member.

6. The apparatus of claim 1, wherein the upright member defines a longitudinal axis, wherein the frame is movable along a dimension that is transverse to the longitudinal axis of the upright member.

7. The apparatus of claim 1, further comprising a headrest secured to the upright member, wherein the headrest is adapted to support a patient's head partially surrounded by the frame.

8. The apparatus of claim 1, wherein the mechanism adapted for removably attaching the supplemental backrest body to the chair comprises a plurality of tabs extending laterally relative to the body.

9. The apparatus of claim 8, wherein the tabs include a plurality of slots configured to receive straps.

10. The apparatus of claim 1, wherein the body, the upright member, and the frame consist of non-metallic materials.

11. The apparatus of claim 1, further comprising a chair, wherein the chair comprises a bottom support and a backrest, wherein the body is positioned above the bottom support, wherein the body is engaged with the backrest.

12. The apparatus of claim 11, wherein the mechanism adapted for removably attaching the supplemental backrest body to the chair comprises at least one strap securing the body to the backrest.

13. The apparatus of claim 11, wherein the frame is movable fore and aft relative to the upright member.

14. The apparatus of claim 13, wherein the frame is movable fore and aft relative to the upright member along a range of motion including an aft-most position where a rear surface of the frame is approximately 15 cm from a front surface of the backrest.

15. The apparatus of claim 13, wherein the frame is movable fore and aft relative to the upright member along a range of motion including a fore-most position where a rear surface of the frame is approximately 25 cm from a front surface of the backrest.

16. The apparatus of claim 1, further comprising an image guided surgery navigation system, wherein the field generating elements are coupled with the image guided surgery navigation system.

* * * * *